US008125645B2

(12) United States Patent
Ozawa

(10) Patent No.: US 8,125,645 B2
(45) Date of Patent: Feb. 28, 2012

(54) OPTICAL TOMOGRAPHIC IMAGING SYSTEM, TOMOGRAPHIC IMAGE ACQUIRING METHOD, AND OPTICAL TOMOGRAPHIC IMAGE FORMING METHOD

(75) Inventor: Satoshi Ozawa, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 452 days.

(21) Appl. No.: 12/414,371

(22) Filed: Mar. 30, 2009

(65) Prior Publication Data
US 2009/0244547 A1 Oct. 1, 2009

(30) Foreign Application Priority Data

Mar. 31, 2008 (JP) ................................ 2008-093712
Mar. 31, 2008 (JP) ................................ 2008-094317

(51) Int. Cl.
*G01B 9/02* (2006.01)
(52) U.S. Cl. .................................................. 356/477
(58) Field of Classification Search .................. None
See application file for complete search history.

(56) References Cited

U.S. PATENT DOCUMENTS 7,633,623 B2 * 12/2009 Hatori ........................... 356/450
7,796,270 B2 * 9/2010 Yelin et al. .................... 356/456

FOREIGN PATENT DOCUMENTS

JP 2003-516531 A 5/2003
WO 01/42735 A1 6/2001

* cited by examiner

*Primary Examiner* — Tu Nguyen
(74) *Attorney, Agent, or Firm* — Sughrue Mion, PLLC

(57) ABSTRACT

This optical tomographic imaging system comprises an optical path length adjustor configured to set a first reference position of a measurement depth direction to an inner edge of a measurement range by adjusting an optical path length of a reference light, and an optical path length switching unit having a preset optical path length that provides a second reference position differing in measurement depth from the first reference position by a predetermined amount and configured to change the optical path length of the reference light or the optical path length of the reflected light adjusted by the optical path length adjustor so as to switch between the first reference position and the second reference position. This system is capable of measuring a measurement region of interest at high resolution, regardless of the position (depth) of the measurement region of interest, in an SS-OCT employing a wavelength-swept light source.

36 Claims, 16 Drawing Sheets

FIG. 2
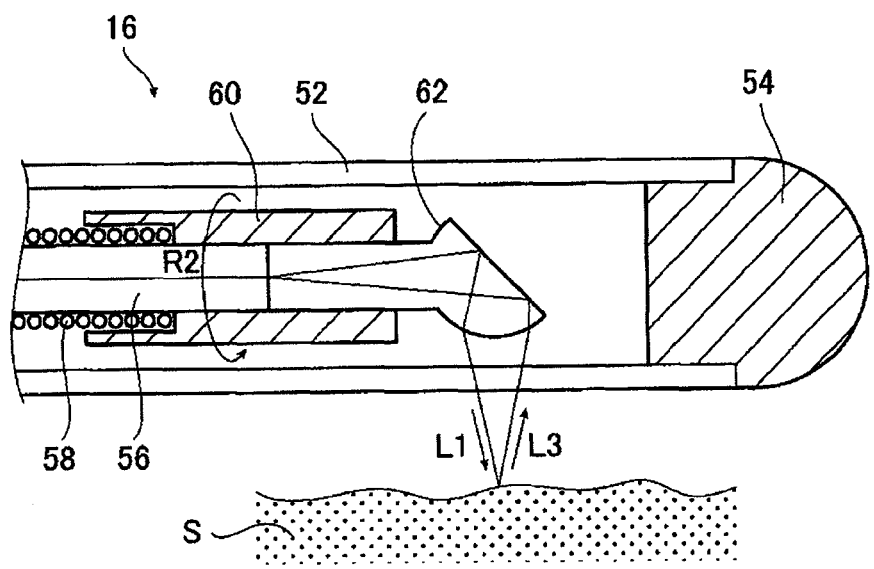
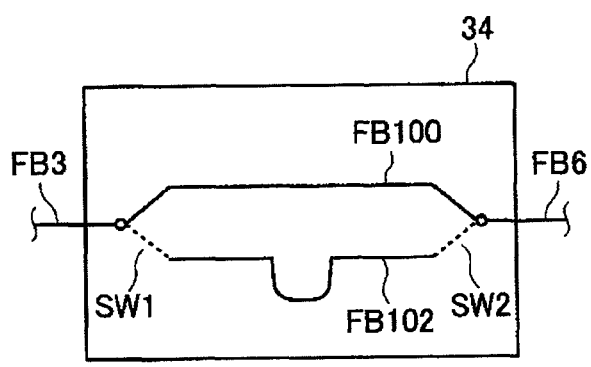
FIG. 3A
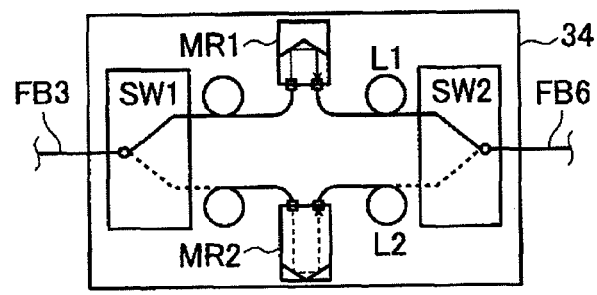
FIG. 3B
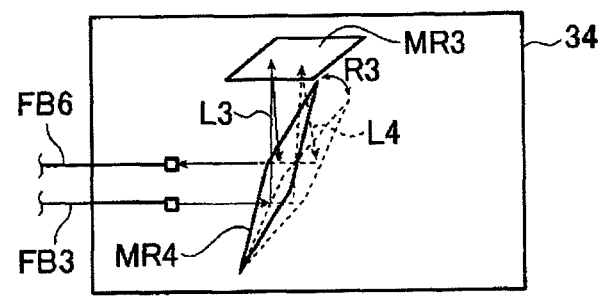
FIG. 3C

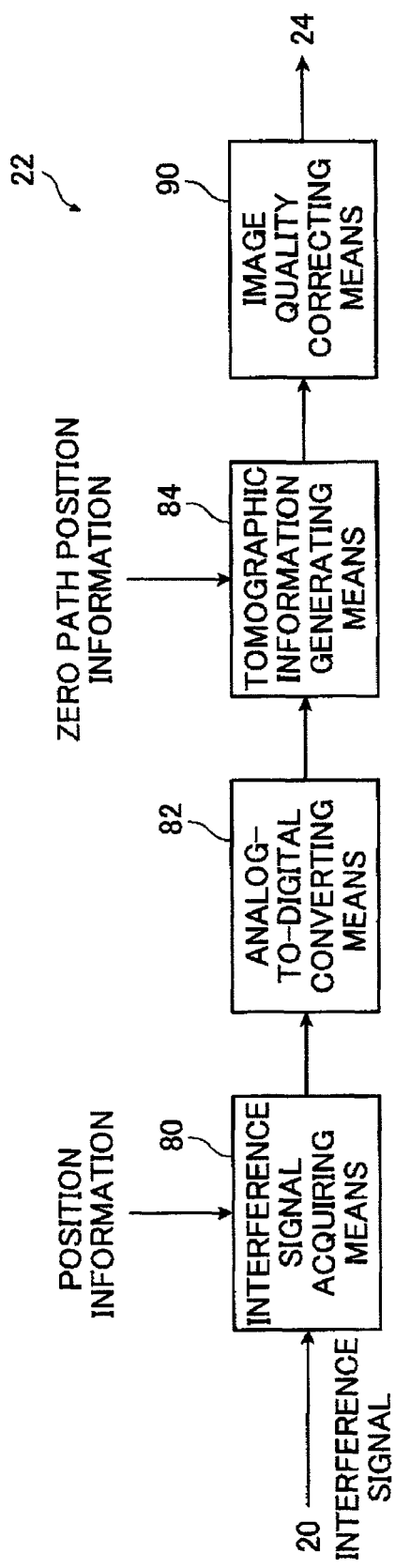

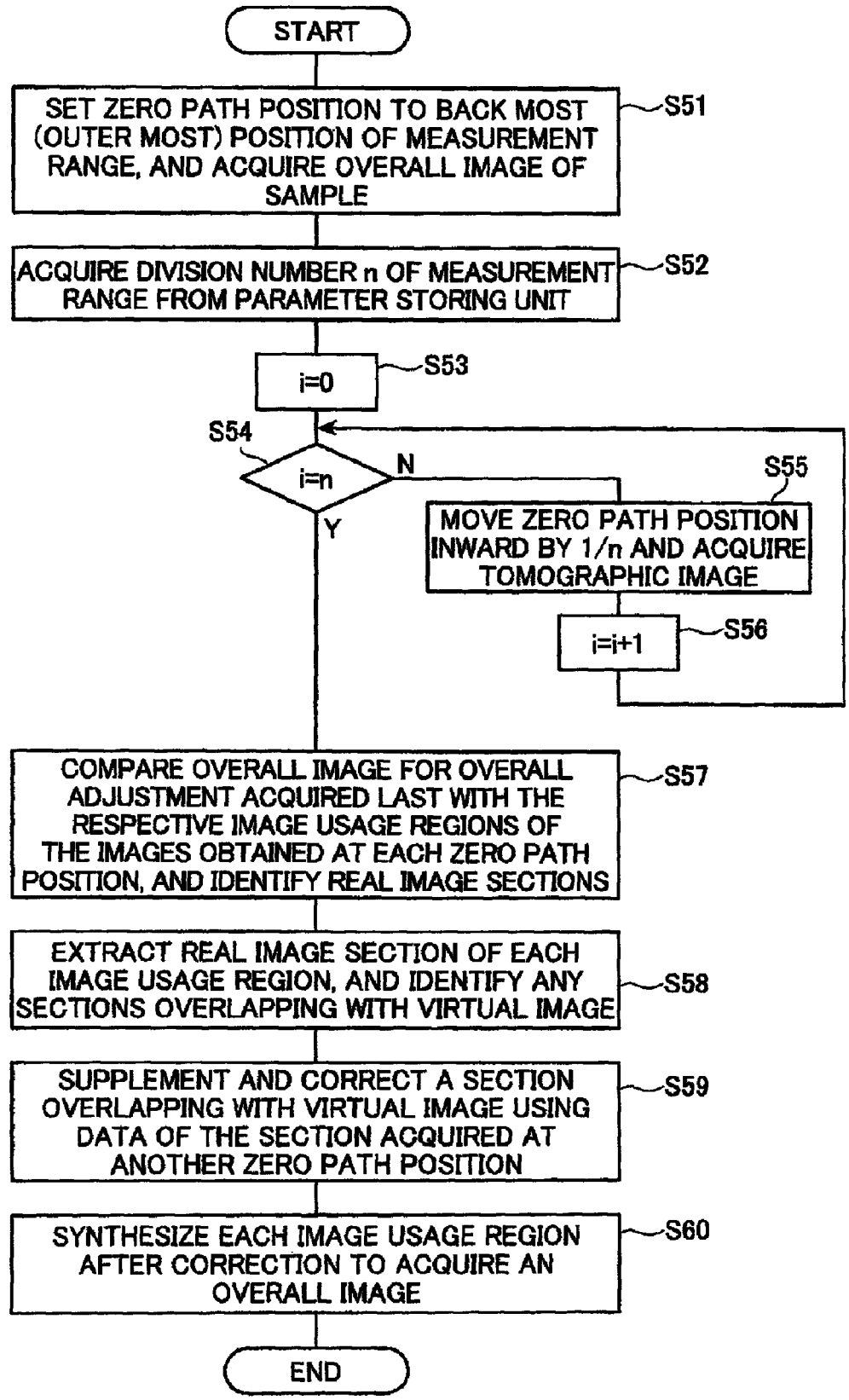

OPTICAL TOMOGRAPHIC IMAGING SYSTEM, TOMOGRAPHIC IMAGE ACQUIRING METHOD, AND OPTICAL TOMOGRAPHIC IMAGE FORMING METHOD

The entire content of a document cited in this specification is incorporated herein by reference.

BACKGROUND OF THE INVENTION

The present invention relates to an OCT optical tomographic imaging system, tomographic image acquiring method, and optical tomographic image forming method that employ a wavelength-swept light source.

Acquisition of a cross-sectional image of a measuring object, i.e., an object to be measured, such as biological tissue without cutting thereinto may be achieved using an optical tomographic imaging system employing optical coherence tomography (OCT) measuring.

The OCT measuring is a kind of optical interferometric measurement using the optical interference that occurs only when the optical path lengths of the measuring light and the reference light, into which the light from the light source is divided, are matched to within the coherence length of the light from the light source.

Known optical tomographic imaging systems include systems that are based on Time Domain OCT (TD-OCT), which obtain a tomographic image by changing the optical path length of the reference light so as to vary the measuring position (measured depth) of the measuring object, and systems based on Spectral Domain OCT (SD-OCT) and Swept Source OCT (SS-OCT), which obtain a tomographic image in the optical axial direction by measuring the intensity of the interference light of each frequency component so as to obtain the Fourier transform of the spectral interference waveform, rather than by changing the optical path length of the reference light.

SS-OCT employing a wavelength-swept light source adjusts the reference position (zero path position) where the optical path lengths of a signal light (measuring light) from a target object and reference light match so that the reference position falls within a desired measurement range within the coherence length of the light source and, once the zero path position is adjusted, fixes the zero path position to that position. With this arrangement, the interference signal is then detected, the Fourier transform of the detected interference signal is obtained, and the absolute value of each characteristic best frequency is plotted, thereby acquiring a tomographic image without changing the optical path length.

In particular, in the SS method and TD method, the measurement range that can be acquired at the same time is limited to within the coherence length of the light source. To this end, for example, JP 2003-516531 A, addresses the OCT system used in a funduscopy apparatus and the difficulties that arise in interpretation in comparison to a conventional Scanning Laser Ophthalmoscope (SLO) due to the short coherence length and the resultant OCT horizontal images that show only segments of the retina, and proposes an optical mapping system that creates a horizontal image by employing an OCT that uses a light source having an extremely short coherence length of a range from 10 µm to 300 µm, changing a reference optical path in stages so as to collect horizontal OCT images of different depths, and then processing the collected horizontal OCT images with software.

This technology attempts to obtain an OCT image across an immeasurable range based on a single measurement by changing the reference optical path in stages and collecting OCT images.

SUMMARY OF THE INVENTION

In the case of an OCT (SS-OCT) that uses a light source having a sufficiently long coherence length, the object under measurement can be grasped by a single measurement.

However, even within a range that is measurable based on a single measurement, the problem arises that the characteristics of a low-coherent light cause the interference intensity to decrease as the distance to the zero path position increases, resulting in an inferior image. For example, in a case of a medical diagnostic image, the depth of a measurement region of interest differs according to the area subject to diagnosis and related circumstances, resulting in cases where sufficient image quality is not obtained when the measurement region of interest is far from the zero path position.

Further, in a case where the measurement region of interest includes a wide range of different depths or is scattered across a range of different depths, the resolution of one region may be high while the resolution of another region may be low, depending on the distance from the zero path position, resulting in cases where it is difficult to obtain a high resolution image at once for all measurement regions of interest.

It is therefore a first object of the present invention to resolve the above problems of prior art and provide an optical tomographic imaging system and tomographic image acquiring method capable of measuring a measurement region of interest at high resolution regardless of the position (depth) of the measurement region of interest using an SS-OCT employing a wavelength-swept light source having a long coherence length in comparison to an SD-OCT.

Further, it is therefore a second object of the present invention to resolve the above problems of prior art and provide an optical tomographic image forming method and optical tomographic imaging system capable of measuring a measurement region of interest covering an entire area of a measurable range based on a single measurement so as to obtain a tomographic image displayed at high resolution across the entire region, using an SS-OCT employing a wavelength-swept light source.

In order to solve the above-described problems and to attain the first object, a first aspect of the present invention provides an optical tomographic imaging system comprising: a wavelength-swept light source; a splitter configured to split light emitted from the wavelength-swept light source into measuring light and reference light; an optical probe configured to irradiate the measuring light from the splitter onto a measuring object to be measured and contain within a sheath a measuring unit that acquires reflected light from the measuring object; an optical path length adjustor configured to set a first reference position of a measurement depth direction to an inner edge of a measurement range by adjusting an optical path length of the reference light; an optical path length switching unit that has a preset optical path length that differs from the first reference position in terms of measurement depth by a predetermined amount and provides a second reference position on an outer edge of the measurement range, and is configured to change the optical path length of the reference light or the optical path length of the reflected light adjusted by the optical path length adjustor so as to switch between the first reference position and the second reference position; a control unit configured to control the optical path length adjustor and the optical path length switching unit; a multiplexer configured to multiplex a reflected light and the reference light acquired by the measuring unit and generate an interference light, disposed on a downstream side of the optical path length adjustor and the optical path length switching unit; an interference light detector configured to detect the interference light generated by the multiplexer as an interference signal; and a tomographic image acquiring and processing unit configured to obtain a tomographic image from the interference signal detected by the interference light detector.

Preferably, the control unit switches the optical path length switching unit to the first reference position and the second reference position during measurement by the measuring unit; and the tomographic image acquiring and processing unit acquires two tomographic images for an identical measuring object based on both the first reference position and the second reference position switched by the optical path length switching unit.

Preferably, the control unit switches the optical path length switching unit to the first reference position and the second reference position in synchronization with a rotational scanning period or a flatbed scanning period of the measuring unit during measurement by the measuring unit; and the tomographic image acquiring and processing unit synthesizes an entire tomographic image or a part of the first reference position side of a tomographic image based on the first reference position, and an entire tomographic image or a part of the second reference position side of a tomographic image based on the second reference position so as to obtain a synthesized tomographic image.

Preferably, the optical path length switching unit comprises plural optical path lengths as the optical path length that provide the second reference position.

And, it is preferable that the optical tomographic imaging system further comprise: a parameter storing unit configured to maintain parameters of the second reference position preset per measurement area; wherein: the control unit reads parameters of the second reference position from the parameter storing unit in accordance with inputted measurement area information, and switches the optical path length of the optical path length switching unit in accordance with the read parameters.

Preferably, the parameter storing unit stores plural parameters as one set of measurement area information; and the control unit reads the parameters of the second reference position in accordance with inputted instruction information, and switches the optical path length of the optical path length switching unit in accordance with the read parameters.

Preferably, the tomographic image acquiring and processing unit further comprises a detector configured to detect a distance between a tip of the optical probe and the measuring object; and the control unit switches the optical path length the optical path length switching unit to an optical path corresponding to the first reference position when a distance between the tip of the optical probe and the measuring object that was detected by the tomographic image acquiring and processing unit is greater than or equal to a predetermined distance.

Preferably, the control unit adjusts the optical path length of the optical path length switching unit or the optical path length adjustor so that the first reference position aligns with a front surface of the measuring object that is nearest to an inner edge of the measurement range when the distance between the tip of the optical probe and the measuring object that is detected by the tomographic image acquiring and processing unit is greater than or equal to a predetermined distance.

Preferably, the optical probe further comprises a drive unit configured to rotate the measuring unit and an optical fiber configured to transmit the measuring light to the measuring unit and the reflected light from the measuring unit; and the tomographic image acquiring and processing unit is configured to obtain a two-dimensional tomographic image of a circular shape corresponding to rotation of the measuring unit and, from an adjustment amount of the first reference position and a distance between the first reference position after adjustment and a center of a tomographic image obtained at the first reference position before adjustment, correct a tomographic image obtained based on the first reference position after the adjustment.

Preferably, the optical path length switching unit further has plural optical paths of different lengths and switching means for switching the plural optical paths.

And, preferably, the optical path length switching unit shifts optical path length adjusting means of the optical path length adjustor so as to switch the optical path to one of plural optical path lengths.

In addition, in order to solve the above-described problems and to attain the first object, a second aspect of the present invention provides a tomographic image acquiring method in the optical tomographic imaging system comprising: switching, when the first reference position or the second reference position is selected in accordance with a measurement region of interest, the optical path length switching unit to the selected reference position; and acquiring a tomographic image based on the switched reference position.

Preferably, a tomographic image acquiring method according to the second aspect of the present invention in the optical tomographic imaging system according to the first aspect comprises: switching the optical path length switching unit to each of the first reference position and the second reference position during measurement by the measuring unit; and acquiring two tomographic images for the same measuring object based on both the first reference position and the second reference position.

It is preferable that the optical tomographic image acquiring method further comprise: switching the optical path length switching unit to each of the first reference position and the second reference position in synchronization with a rotational scanning period or a flatbed scanning period of the measuring unit, during measurement by the measuring unit; and synthesizing a part of the first reference position side of a tomographic image based on the first reference position and a part of the second reference position side of a tomographic image based on the second reference position so as to obtain a synthesized tomographic image.

It is preferable that a tomographic image acquiring method according to the second aspect of the present invention in the optical tomographic imaging system according to the first aspect further comprise: reading parameters of the second reference position from the parameter storing unit based on inputting of measurement area information; and switching the optical path length of the optical path length switching unit in accordance with the read parameters.

It is preferable that the optical tomographic image acquiring method further comprise the steps of: detecting a distance between the tip of the optical probe and the measuring object; and automatically selecting the first reference position when a detected distance between a tip of the optical probe and the measuring object is greater than or equal to a predetermined distance.

It is preferable that the tomographic image acquiring method further comprise a step of adjusting the optical path length adjustor so that the first reference position is aligned with a front surface of the measuring object that is nearest to an inner edge of the measurement range when a detected distance between the tip of the optical probe and the measuring object is greater than or equal to a predetermined distance.

It is preferable that the tomographic image acquiring method further comprise the step of correcting, from an adjustment amount of the first reference position and a distance between the first reference position after adjustment and a center of a tomographic image obtained at the first reference position before adjustment, a tomographic image obtained based on the first reference position after the adjustment so as to generate an image similar to a tomographic image obtained at the first reference position before adjustment, in a case where a two-dimensional tomographic image of a circular shape corresponding to rotation of the measuring unit is to be obtained.

And, in order to solve the above-described problems and to attain the second object, a third aspect of the present invention provides an optical tomographic image forming method based on optical tomographic image measurement using a wavelength-swept light source, comprising: setting a first reference position of a measurement depth direction to an inner edge or an outer edge of a measurement range; setting plural reference positions, each having a measurement depth differing from that of the first reference position; acquiring plural tomographic images based on the first reference position and the plural reference positions for the same measuring object; and synthesizing regions of the plural tomographic images in whole or in part so as to form a single synthesized tomographic image.

Preferably, the step of synthesizing the plural tomographic images includes the synthesizing of regions near the reference position of each tomographic image.

It is preferable that the optical tomographic image forming method, after the plural tomographic images based on the plural reference positions are acquired, further comprise: identifying for each of the plural tomographic images a false signal included in the signal of the tomographic image, based on the signal of a region on the side opposite the reference position; obtaining a real signal by removing the false signal from the signal of the tomographic image; generating a real image by the real signal of the tomographic image; and forming the synthesized tomographic image using the real images of the plural tomographic images.

Preferably, the step of identifying the false signal is performed by comparing each of plural tomographic images based on the plural reference positions with a tomographic image based on the first reference position, and identifying a signal that does not exist in a tomographic image based on the first reference position as a false signal.

Preferable, the step of identifying the false signal is performed by comparing two of the tomographic images based on the reference positions located next to each other, and identifying a signal that moves an amount equivalent to double an amount of shift of the reference position in the same direction as the direction of shift of the reference position, or a signal other than a signal that shifts in the direction opposite the direction of shift of the reference position as a false signal.

It is preferable that the optical tomographic image forming method further comprise the step of weighting the plural tomographic images in whole or in part, and synthesizing the weighted tomographic images.

And, preferably, a range of the tomographic image to be used in the synthesized tomographic image is arbitrarily set in accordance with the measuring object.

It is preferable that the optical tomographic image forming method further comprise: reading the position parameters of the plural reference positions corresponding to the inputted measurement area information; and setting the plural reference positions based on the read position parameters, wherein the position parameters of the plural reference positions for acquiring the plural tomographic images are pre-stored per measurement area.

Preferable, the plural reference positions include a second reference position at an outer edge or an inner edge of a measurement range; and the second reference position and the number of the reference positions set between the first reference position and the second reference position are stored as the position parameters.

In order to solve the above-described problems and to attain the second object, a fourth aspect of the present invention provides an optical tomographic imaging system, comprising: a wavelength-swept light source; a splitter configured to split light emitted from the wavelength-swept light source into measuring light and reference light; an optical probe configured to irradiate the measuring light from the splitter onto a measuring object and contain within a sheath a measuring unit that acquires reflected light from the measuring object; an optical path length adjustor configured to set a first reference position of a measurement depth direction to an inner edge of a measurement range by adjusting an optical path length of the reference light; an optical path length switching unit having preset plural optical path lengths that provide plural reference positions that differ from the first reference position in terms of measurement depth, and configured to change the optical path length of the reference light or the optical path length of the reflected light adjusted by the optical path length adjustor so as to switch to the first reference position or one of the plural reference positions; a control unit configured to control the optical path length switching unit so as to switch to the first reference position and one of the plural reference positions in synchronization with a rotational scanning period or a flatbed scanning period of the measuring unit, during measurement by the measuring unit; a multiplexer configured to multiplex a reflected light and the reference light acquired by the measuring unit and generate an interference light, disposed on a downstream side of the optical path length adjustor and the optical path length switching unit; an interference light detector configured to detect the interference light generated by the multiplexer as an interference signal; a tomographic image generator configured to generate plural tomographic images respectively based on the first reference position and the plural reference positions switched by the optical path length switching unit, from the interference signal detected by the interference light detector; and an image synthesizer configured to synthesize the plural tomographic images acquired by the tomographic image generator in whole or in part and form a single synthesized tomographic image.

Preferable, the image synthesizer synthesizes the plural tomographic images so as to include regions near the reference position of each tomographic image.

Preferable, the tomographic image generator identifies for each of plural tomographic images based on the plural reference positions a false signal that is included in the signal of the tomographic image and is based on the signal of a region on the side opposite the reference position, and generates a real image by a real signal after the false signal is removed from the signal of the tomographic image; and the image synthesizer synthesizes the plural tomographic images using the real images of the plural tomographic images generated by the tomographic image generator.

Preferably, the tomographic image generator identifies the false signal by comparing each of plural tomographic images based on the plural reference positions with a tomographic image based on the first reference position, and identifying a signal that does not exist in a tomographic image based on the first reference position as a false signal.

Preferably, the tomographic image generator identifies the false signal by comparing two of the tomographic images based on the reference positions located next to each other, and identifying a signal that moves an amount equivalent to double the amount of shift of the reference position in the same direction as the direction of shift of the reference position, or a signal other than a signal that shifts in the direction opposite the direction of shift of the reference position as a false signal.

Preferably, the image synthesizer weights the plural tomographic images in whole or in part, and synthesizes the weighted tomographic images.

And, preferably, the range of the tomographic image to be used in the synthesized tomographic image is arbitrarily set in accordance with a measuring object.

It is preferable that the optical tomographic imaging system further comprise a parameter storing unit configured to store position parameters of the plural reference positions preset per measurement area, wherein: the control unit reads the position parameters of the plural reference positions from the parameter storing unit in accordance with inputted measurement area information, and switches the optical path length of the optical path length switching unit in accordance with the read position parameters.

Preferably, the plural reference positions include a second reference position at an outer edge or an inner edge of a measurement range, and the parameter storing unit stores as the position parameters the second reference position and the number of the reference positions between the first reference position and the second reference position.

According to the first and second aspects of the present invention, a measurement region of interest is measured at high resolution regardless of the position (depth) of the measurement region of interest by using an SS-OCT that employs a wavelength-swept light source and establishing a configuration wherein the reference position (zero path position) of measurement can be switched between the inside and the outside of the measurable range.

Further, in a preferred embodiment of the present invention, images obtained from measurements taken upon switching the zero path position between the inside and the outside of the measurable range are synthesized, making it possible to obtain a high-resolution image across the entire measurable range.

Further, in a preferred embodiment of the present invention, the parameters of the zero path position are prepared for each measurement area, making it possible for an operator to simply input information that indicates the location of the measurement area (measurement area information) so that the system automatically switches and measures the zero path position instantaneously, thereby speeding up measurement and enhancing system user-friendliness.

Furthermore, according to a preferred embodiment of the present invention, when the probe of the measurement device is detected as being a certain distance or greater away from the object under measurement (hereinafter "object"), the zero path position is automatically switched to inside the measurable range and aligned to the front surface of the object that is closest to the probe, making it possible to increase the resolution near the front surface of the displayed image and easily grasp the overall shape, thereby improving measurement friendliness.

Further, according to the third aspect and the fourth aspect of the present invention, an SS-OCT employing a wavelength-swept light source comprises a configuration that makes it possible to switch the measurement reference position (zero path position) a plurality of times within the measurable range during measurement of the same object, and forms a single synthesized tomographic image that synthesizes the tomographic images obtained at the plurality of zero path positions, thereby making it possible to measure a measurement region of interest at high resolution regardless of its location within the measurable range. This also makes it possible to obtain a high-resolution image across the entire region of the image depth.

Further, according to a preferred embodiment of the present invention, when the zero path position is set and measured in an intermediate region of the measurable range and a false signal is included in the measurement signals, that false signal is identified and the real image section is extracted, thereby making it possible to measure the entire region of the measurable range at high resolution regardless of the position (depth) of the measurement region of interest.

Further, in a preferred embodiment of the present invention, the position parameters of the zero path position are prepared for each measurement area, making it possible for an operator to simply input information that indicates the location of the measurement area (measurement area information) so that the system automatically switches to and measures a predetermined plurality of zero path positions instantaneously, thereby speeding up measurement and improving system user-friendliness.

BRIEF DESCRIPTION OF THE INVENTION

FIG. 2 is a partial, sectional view illustrating an optical probe of the optical tomographic imaging system of FIG. 1, with the tip of the optical probe shown enlarged.

FIG. 3A to FIG. 3C are views schematically illustrating a configuration example of the optical path length switching unit of the optical tomographic imaging system of FIG. 1.

FIG. 4 is a block diagram schematically illustrating the configuration of an embodiment of the processor in the optical tomographic imaging system of FIG. 1.

FIG. 21 is a flowchart illustrating a tomographic image forming method of the seventh embodiment of the present invention.

DETAILED DESCRIPTION OF THE INVENTION

An optical tomographic imaging system, tomographic image acquiring method, and optical tomographic image forming method according to the present invention will now be described in detail based on the preferred embodiments shown in accompanying drawings.

First, the optical tomographic imaging system according to the first aspect and the tomographic image acquiring method according to the second aspect of the present invention will be described with reference to FIG. 1 to FIG. 12.

First, the first embodiment of an optical tomographic imaging system of the first aspect of the present invention will be described.

Figure 1:
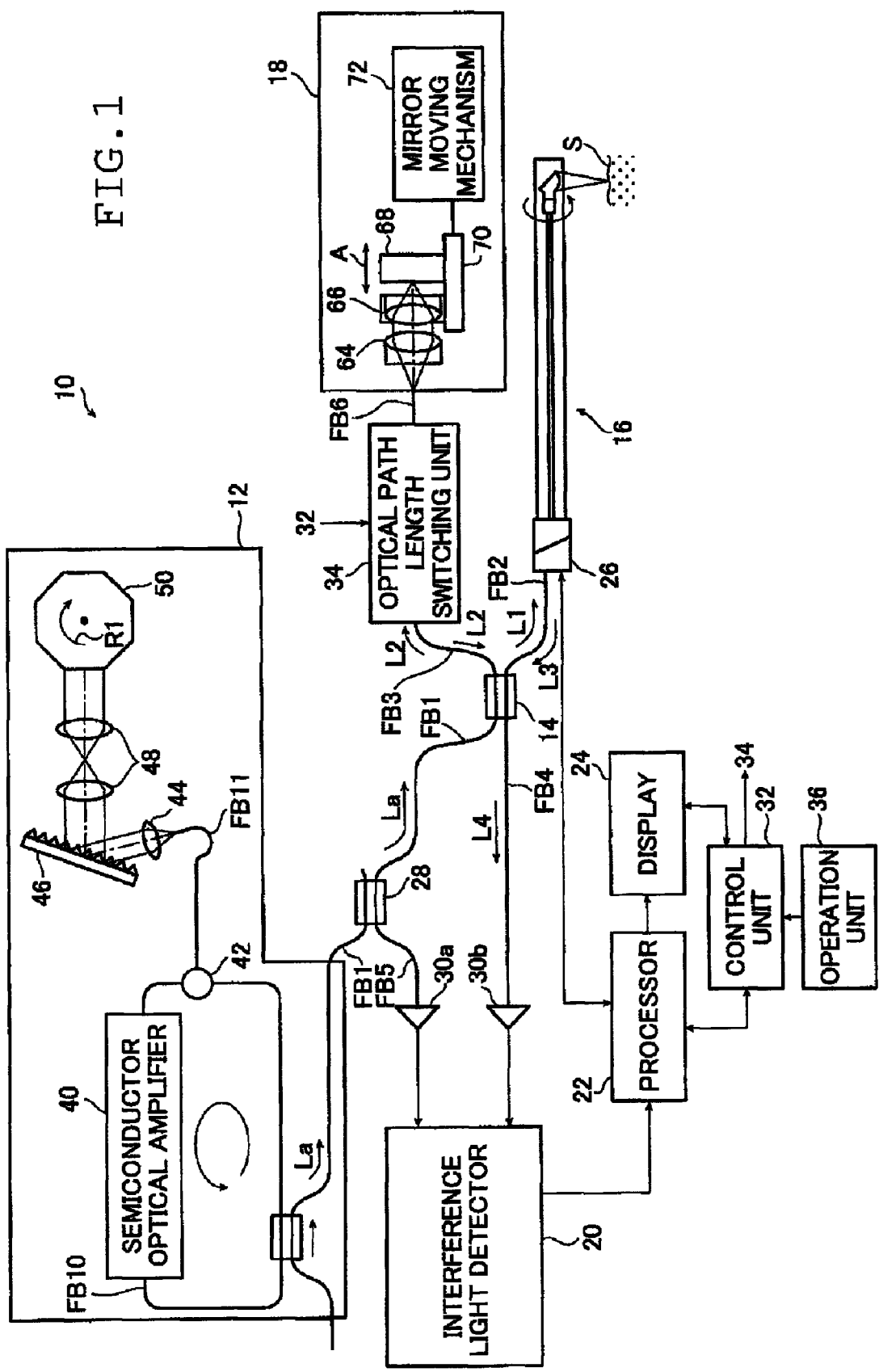
FIG. 1 is a block diagram schematically illustrating the configuration of an embodiment of an optical tomographic imaging system according to the present invention.

FIG. 1 is a block diagram schematically illustrating the configuration of the first embodiment of an optical tomographic imaging system of the first aspect of the present invention, which implements a tomographic image acquiring method of the second aspect of the present invention. An optical tomographic imaging system 10 shown in FIG. 1 is a so-called Swept Source OCT (SS-OCT) that uses a wavelength-swept light source to scan an object with measuring light and obtain a reflected light so as to obtain a tomographic image of the optical axial direction of the measuring light based on the reflected light, reference light, and interference light.

The optical tomographic imaging system 10 comprises: a light source unit 12 configured to emit light, a splitting multiplexer 14 configured to split the light emitted from the light source unit 12 into a measuring light and a reference light and multiplex the reflected light of the measuring light that is reflected from the object and the reference light to generate an interference light, an optical probe 16 configured to guide and irradiate the measuring light onto the object and receive the reflected light from the object, an optical path length adjustor 18 configured to adjust the optical path length of the reference light, an optical path length switching unit 34 configured to selectively switch the optical path length to an optical path length that differs from the optical path length of the reference light, an interference light detector 20 configured to detect the interference light generated by the splitting multiplexer 14 as an interference signal, a processor 22 configured to process the interference signal detected by the interference light detector 20, a display 24 configured to display the optical tomographic image (hereinafter simply "tomographic image") acquired by the processor 22, a control unit 32 configured to control the entire optical tomographic imaging system 10 including the optical path length adjustor 18 and the optical path length switching unit 34, and an operation unit 36 configured to receive an instruction input for inputting or changing various conditions from an external source, for example.

The optical tomographic imaging system 10 further comprises: a rotary drive unit 26 configured to rotate the measuring unit of the optical probe for the rotational scanning of the measuring light, an optical fiber coupler 28 configured to disperse the light emitted from the light source unit 12, a detector 30a configured to detect the light of the light source (laser light), and a detector 30b configured to detect the reflected light. Further, the optical tomographic imaging system 10 uses an optical fiber FB as an optical path between components to guide a light source light (laser light) La, a measuring light L1, a reference light L2, a reflected light L3, and an interference light L4 to each part. Each part will now be described in detail.

The light source unit 12 comprises a semiconductor optical amplifier 40, an optical splitter 42, a collimating lens 44, a diffraction grating element 46, an optical system 48, and a rotary polygon mirror 50 and emits the laser beam La that is frequency-swept with a constant period.

The semiconductor optical amplifier (semiconductor gain medium) 40 emits feeble light upon application of drive current and amplifies incoming light. Both ends of an optical fiber FB10 are connected to the semiconductor optical amplifier 40 to form a loop. That is, one end of the optical fiber FB10 is connected to a part of the semiconductor optical amplifier 40 at which light is emitted, whereas the other end of the optical fiber FB10 is connected to a part of the semiconductor optical amplifier 40 at which light enters. The light emitted from the semiconductor optical amplifier 40 is emitted to the optical fiber FB10 and re-enters the semiconductor optical amplifier 40. Thus, the semiconductor optical amplifier 40 and the optical fiber FB10, forming an optical path loop, provide an optical resonator. Application of driving current to the semiconductor optical amplifier 40 causes a pulse laser beam to be generated.

The optical splitter 42 is provided on the optical path of the optical fiber FB10 and also connected with an optical fiber FB11. The optical splitter 42 directs part of the light guided through the optical fiber FB10 to the optical fiber FB11. The collimating lens 44 is disposed at the other end of the optical fiber FB11, i.e., near the end thereof not connected with the optical fiber FB10, and collimates the light emitted from the optical fiber FB11. The diffraction grating element 46 is disposed with a given inclination angle on the optical path of the parallel light produced by the collimating lens 44. The diffraction grating element 46 disperses the parallel light emitted from the collimating lens 44.

The optical system 48 is disposed on the optical path of the light dispersed by the diffraction grating element 46. The optical system 48 comprises a plurality of lenses to refract the light dispersed by the diffraction grating element 46 and collimate the refracted light. The rotary polygon mirror 50 is disposed on the optical path of the parallel light produced by the optical system 48 to reflect the parallel light. The rotary polygon mirror 50 is a rotating body that rotates at a constant speed in direction R1 in FIG. 1. The surface of the rotary polygon mirror 50 that is orthogonal to the axis of rotation is a regular octagon, and the side surface of the rotary polygon mirror 50 on which the parallel light is irradiated (the surface comprising each side of the octagon) comprises a reflection surface that reflects the irradiated light. The rotary polygon mirror 50 turns to vary the angle of the reflection surfaces with respect to the optical axis of the optical system 48.

The light emitted from the optical fiber FB11 passes through the collimating lens 44, the diffraction grating element 46, and the optical system 48 and is reflected by the rotary polygon mirror 50. The returned light passes through the optical system 48, the diffraction grating element 46, and the collimating lens 44 and enters the optical fiber FB11.

Since the angle of the reflection surfaces of the rotary polygon mirror 50 varies with respect to the optical axis of the optical system 48 as described above, the angle at which the rotary polygon mirror 50 reflects the light varies with time. Accordingly, only the light having a particular frequency range among the light dispersed by the diffraction grating element 46 re-enters the optical fiber FB11. Thus, since the light having a particular frequency range entering the optical fiber FB11 is determined by the angle formed by the optical axis of the optical system 48 and the reflection surface of the rotary polygon mirror 50, the frequency range of the light entering the optical fiber FB11 varies with the angle formed by the optical axis of the optical system 48 and the reflection surface of the rotary polygon mirror 50.

The light having a particular frequency range allowed to enter the optical fiber FB11 is delivered through the optical splitter 42 to the optical fiber FB10 and multiplexed with the light of the optical fiber FB10. Thus, the pulse laser beam guided to the optical fiber FB10 becomes a laser beam having a particular frequency range and this laser beam La having a particular frequency range is emitted to the optical fiber FB1. Since the rotary polygon mirror 50 is turning at a constant speed in the direction indicated by the arrow R1, the wavelength λ the light re-entering the optical fiber FB11 varies with a constant period as time passes. Accordingly, the frequency of the laser beam La emitted to the optical fiber FB1 also varies with a constant period as time passes.

The light source unit 12 is configured as described above and emits the wavelength-swept laser light La to the optical fiber FB1.

Next, the splitting multiplexer 14 is formed, for example, by a 2×2 optical fiber coupler and optically connected to an optical fiber FB1, an optical fiber FB2, an optical fiber FB3, and an optical fiber FB4.

The splitting multiplexer 14 splits the incoming light La delivered from the light source unit 12 through the optical fiber FB1 into the measuring light L1 and the reference light L2, directing the measuring light L1 to the optical fiber FB2 and the reference light L2 to the optical fiber FB3. Further, the splitting multiplexer 14 multiplexes the reference light L2 delivered to the optical fiber FB3, returned through the optical fiber FB3 via the optical path length switching unit 34 and the optical path length adjustor 18, and once again delivered to the splitting multiplexer 14, and the reflected light L3 from the object S that was acquired by the optical probe 16 based on the measuring light L1 delivered to the optical fiber FB2, returned through the optical fiber FB2, and once again delivered to the splitting multiplexer 14.

The optical probe 16 is an instrument configured to measure an object S upon insertion into a body to be inspected. The rear end part of the optical probe 16 is connected to the optical fiber FB2 so that the measuring light L1 from the optical fiber FB2 is guided to the tip thereof and irradiated on the object S at the measuring unit of the tip, and the reflected light L3 from the object S is received. Further, the measuring unit of the optical probe 16 is rotated by the rotary drive unit 26, causing the measuring light L1 to rotationally scan around the axis of the optical probe 16.

FIG. 2 shows an enlarged cross-sectional view of the tip of the optical probe 16. As shown in FIG. 2, the optical probe 16 comprises a probe sheath 52, a cap 54 configured to cover the tip of the probe sheath 52, an optical fiber 56, a flexible shaft 58, a fixing member (sleeve) 60, and an optical lens 62.

The probe sheath 52 is a cylindrical member having flexibility, with at least the section of the tip thereof through which the measuring light L1 and the reflected light L3 pass is formed out of a material that transmits light (a transparent material).

The optical fiber 56 is inserted into the interior of the probe sheath 52, with the rear end thereof connected to the optical fiber FB2 and the tip end thereof connected to the optical lens 62, which becomes the measuring unit. The optical fiber 56 guides the measuring light L1 emitted from the optical fiber FB2 to the optical lens 62, and guides the reflected light L3 from the object S for the measuring light L1 acquired by the optical lens 62 to the optical fiber FB2.

The optical lens 62 is optically connected to the tip end of the optical fiber 56. The optical lens 62 is a so-called hemispherical lens that focuses the measuring light L1 emitted from the optical fiber 56 onto the object S. The optical lens 62 also focuses the reflected light L3 of the measuring light L1 of the object S, directing the reflected light L3 to the optical fiber 56.

The connected section of the tip end of the optical fiber 56 and the optical lens 62 is held by the fixing member 60, and the flexible shaft 58 is provided on this fixing member 60. The flexible shaft 58 contains the optical fiber 56 in its hollow, and extends to the rear end part of the probe sheath 52. The rear end part of the flexible shaft 58 is connected to the rotary drive unit 26. The rotary drive unit 26 drives the rotation of the flexible shaft 58, thereby rotating the optical fiber 56 and the optical lens 62 with respect to the probe sheath 52, in the direction of arrow R2 in FIG. 2, for example.

The optical fiber 56 is supported rotatably in relation to the probe sheath 52.

The optical fiber 56 and the optical fiber FB2 are connected by a rotary joint or the like; they are optically connected such that the rotation of the optical fiber 56 is not conveyed to the optical fiber FB2.

The rotary drive unit 26 has a rotary encoder (not shown) to detect the irradiation position of the measuring light L1 according to the position information (angular information) on the optical lens 62 based on the signal given by the rotary encoder, and send the detected irradiation position as position information to the processor 22.

The optical probe 16 is basically configured as described above. As the rotary drive unit 26 turns the optical fiber 56 and the flexible shaft 58 in the direction indicated by the arrow R2 in FIG. 2, the optical probe 16 irradiates the object S with the measuring light L1 emitted from the optical lens 62 by scanning in the direction indicated by the arrow R1 in FIG. 2 (in the circumferential direction of the probe sheath 52) and acquires the reflected light L3. Thus acquired is the reflected light L3 for the whole circumference of the probe sheath 52 as it is reflected by the object S.

The optical path length adjustor 18 is a section that adjusts the optical path length of the reference light L2. This optical path length adjustor 18 is connected to the splitting multiplexer 14 and to an optical fiber FB3, which is the guiding path of the reference light L2 split from the laser light La, via the optical path length switching unit 32. The optical path length adjustor 18 and the optical path length switching unit 32 are connected by an optical fiber FB6.

The optical path length adjustor 18 comprises a first optical lens 64 configured to collimate the reference light L2 emitted from the optical fiber FB6, a second optical lens 66 configured to focus the light thus collimated by the first optical lens 64, a reflecting mirror 68 configured to reflect the light thus focused by the second optical lens 66, a base 70 configured to statically support the second optical lens 66 and the reflecting mirror 68, and a mirror moving mechanism 72 configured to move the base 70 in a direction parallel to the optical axial direction.

The optical path length adjustor 18 adjusts the optical path length of the reference light L2 by changing the distance between the first optical lens 64 and the second optical lens 66, and sets a reference position (hereinafter "zero path position") of the depth of the object to be measured by the measuring light L1.

The first optical lens 64 collimates the reference light L2 emitted from the core of the optical fiber FB6 and focuses the reference light L2 reflected by the reflecting mirror 68 onto the core of the optical fiber FB6. The second optical lens 66 focuses the reference light L2 collimated by the first optical lens 64 onto the reflecting mirror 68 and collimates the reference light L2 reflected by the reflecting mirror 68. Thus, the first optical lens 64 and the second optical lens 66 form a confocal optical system. The reflecting mirror 68 is disposed at the focal point of the light focused by the second optical lens 66 and reflects the reference light L2 focused by the second optical lens 66.

The reference light L2 emitted from the optical fiber FB6 is collimated by the first optical lens 64 and focused by the second optical lens 66 onto the reflecting mirror 68. Subsequently, the reference light L2 reflected by the reflecting mirror 68 is collimated by the second optical lens 66 and focused by the first optical lens 64 onto the core of the optical fiber FB6.

The mirror moving mechanism 72 moves the base 70 in the optical axial direction (in the direction indicated by arrow A in FIG. 1) of the first optical lens 64. The mirror moving mechanism 72 is controlled by the control unit 32 so as to move the base 70 in the optical axial direction, thereby changing the distance between the first optical lens 64 and the second optical lens 66 to adjust the optical path length of the reference light L2.

The optical path length switching unit 34 is a special characteristic of the present invention, and is disposed between the splitting multiplexer 14 and the optical path length adjustor 18. The splitting multiplexer 14 and the optical path length switching unit 34 are connected by the optical fiber FB3, and the optical path length switching unit 34 and the optical path length adjustor 18 are connected by the optical fiber FB6.

The optical path length switching unit 34 comprises a configuration that makes it possible to switch to two preset optical path lengths, and the optical path length is selectively switched based on the control from the control unit 32. The difference between the two optical path lengths is set so that the value is substantially equal to the difference between the maximum value and the minimum value of the depth of the measurable range of the optical tomographic imaging system 10. Thus, when the optical path length is switched by the optical path length switching unit 34 after the zero path position (the reference position of the measurement range in the depth direction) is set by the optical path length adjustor 18 to one optical path length of the optical path length switching unit 34, the zero path position is switched to the edge of the side opposite the measurable range.

When the optical path length is switched, the optical path length switching unit 34 sends information on the selected optical path, i.e., information on the optical path lengths connected to the optical fibers FB3 and FB6, as zero path information to the control unit 32.

Note that the specific configuration of the optical path length switching unit 34 is not particularly limited as long as the optical path length can be switched to predetermined optical path lengths. The optical path length switching unit 34 may comprise a configuration such as that illustrated below.

For example, the optical path length switching unit 34 may comprise a plurality of optical fibers of different lengths and an optical switch that switches the optical fibers. That is, as shown in FIG. 3A, the optical path length switching unit 34 may comprise two optical fibers FB100 and FB102 having different optical path lengths, an optical switch SW1 that switches the optical path that emits the reference light L2 emitted from the optical fiber FB3 to either the optical fiber FB100 or FB102, and an optical switch SW2 that switches the optical fiber FB100 and the optical fiber FB102 in coordination with the optical switch SW1. With this arrangement, the optical path length switching unit 34 switches the optical switch SW1 and the optical switch SW2, thereby instantaneously switching the optical path length of the reference light L2.

As a result, with the first optical path that is routed through the optical fiber FB100 as switched by the optical switches SW1 and SW2 and the second optical path that is routed through the optical fiber FB102 as switched by the optical switches SW1 and SW2, the optical path length of the reference light L2 is changed by an amount equivalent to the optical path difference between the optical fiber FB100 and the optical fiber FB102.

Additionally, as another example, the optical path length switching unit 34 may be configured using an optical switch capable of selecting a plurality of spatial distances. For example, as shown in FIG. 3B, the optical path length switching unit 34 may be configured to comprise spaces L1 and L2 having different positions of reflecting mirrors MR1 and MR2 and different optical path lengths, and the optical switches SW1 and SW2 that switch the spaces L1 and L2.

Further, the optical path length switching unit 34 may comprise a configuration that switches the spatial length in a non-contact manner. That is, as shown in FIG. 3C, the optical path length switching unit 34 may use the oscillation angle control of a fixed mirror MR3 and an MEMS mirror or galvanic mirror MR4 to oscillate the MEMS mirror or galvanic mirror MR3 to a preset angle R3 and switch the spaces L3 and L4 to switch the spatial length, thereby switching the optical path length in a non-contact manner.

Or, the optical path length switching unit 34 may be configured to switch the optical path length by the high-speed drive of the reflecting mirror. For example, the optical path length adjustor 18 may be used as the optical path length switching unit 34 as well, or the optical path length switching unit 34 may be separately provided using the same configuration as the optical path length adjustor 18 so as to operate at high speed a delay device that uses the mirror moving mechanism 72 and switch the optical path length.

The interference light detector 20 detects as an interference signal the interference light L4 that was generated by the splitting multiplexer 14 by combining the reference light L2 and the reflected light L3. The interference light detector 20 is connected with the splitting multiplexer 14 by the optical fiber FB4. The detector 30$a$ configured to detect the light intensity of a laser beam La split from the optical fiber FB1 to the optical fiber FB5 by the optical fiber coupler 28, and the detector 30$b$ configured to detect the light intensity of the interference light L4 from the splitting multiplexer 14 are connected to the inlet side of the interference light detector 20, and the detection results of the detector 30$a$ and the detector 30$b$ are sent to the interference light detector 20. The interference light detector 20 adjusts the balance of the light intensity of the interference light L4 based on the detection results of the detector 30$a$ and the detector 30$b$.

The processor 22 acquires the tomographic image from the interference signal detected by the interference light detector 20. FIG. 4 schematically illustrates the configuration of the processor 22. As shown in FIG. 4, the processor 22 comprises interference signal acquiring means 80, analog-to-digital converting means 82, tomographic image generating means 84, and image quality correcting means 90.

The interference signal acquiring means 80 acquires the interference signal detected by the interference light detector 20 and the position information on the measuring position detected by the rotary drive unit 26, more specifically, information on the irradiation position of the measuring light L1 detected from the position information of the optical lens 62 in the rotating direction, and correlates the interference signal with the position information on the measuring position.

The interference signal and the position information of the measuring position may be correlated as follows.

First, the measurement count per rotation of the optical lens 62 is determined from the rotational speed of the optical lens 62 and the period at which the frequency of the measuring light L1 is swept. When the rotation of the optical lens 62 and the acquisition count of the interference signal, i.e., the period of sweeping of the measuring light L1, are constant, the position of measuring by the measuring light L1 moves, i.e., shifts, in increments of a predetermined angle centering about the rotational axis of the optical lens 62.

Since the position at which the interference signal is acquired is moved (shifted) in increments of a predetermined angle, a line number n can be correlated with each measuring position of the interference signal. For example, given that the interference signal is acquired 1024 times during one rotation of the optical lens 62, the line numbers n=1 to 1024 can be assigned as the acquisition positions (measuring positions) of the interference signals. Additionally, since the optical lens 62 rotates, the measuring position of n=1024 and the measuring position of n=1 are next to each other. The interference signal correlated with the position information on the measuring position is sent to the analog-to-digital converting means 82.

The analog-to-digital converting means 82 converts to a digital signal the interference signal produced from the interference signal acquiring means 80 as an analog signal correlated with the position information on the measuring position. The interference signal thus converted to a digital signal is sent to the tomographic information generating means 84.

The tomographic information generating means 84 performs FFT (Fast Fourier Transform) processing on the interference signal thus converted to a digital signal by the analog-to-digital converting means 82, acquires information on the relationship between frequency component and intensity, and processes the acquired information, thereby acquiring a tomographic image of the depth direction at each measuring position.

Here, the tomographic information generating means 84 assesses from the interference signal and the zero path position information sent from the control unit 32 whether or not the set zero path position is on the front side of the measuring range (on the shallow side of the measured depth; the inside) as viewed from the optical probe 16, and generates a tomographic image of the depth direction in accordance with the assessment result. If the zero path position is on the front side, the result in the direction toward the back side after FFT processing is used; and if the zero path position is on the back side, the result in the direction toward the center of the optical probe 16, which is on the front side from the zero path position of the back side after FFT processing, is used, thereby making it possible to generate a tomographic image from a suitable interference signal acquired within the measurement range.

The tomographic information generating means 84 can generate an image by using the technology described in the literature by Mitsuo Takeda, "Optical Frequency Scanning Spectrum Interference Microscopes," Optics Engineering Contact, Vol. 41, No. 7, pp. 426-432, 2003. The following provides a simple explanation.

Let S(l) be the light intensity of interference fringes for each optical path length difference l of the various optical path length differences with which the reflected light L3 from the respective depths in the object S interferes with the reference light L2 as the measuring light L1 irradiates the object S. Then, the light intensity I(k) of the interference signal detected in the interference light detector 20 is expressed by an expression:

$$I(k)=\int_0^\infty S(l)[1+\cos(kl)]dl$$

where k is the number of waves and l the optical path length difference. The above expression may be considered to represent an interferogram for an optical frequency range having the number of waves k=ω/c as a variable. Accordingly, in the tomographic information generating means 84, the light intensity S(l) of the interference light L4 may be determined by applying fast Fourier transform to the spectral interference fringes detected by the interference light detector 20, thereby yielding information on the distance from the measurement starting position of the object S as well as information on reflection intensity, and generating a tomographic image.

The image quality correcting means 90 performs logarithmic conversion and radial conversion of the tomographic image generated by the tomographic information generating means 84 to dispose the tomographic image in line number sequence and obtain a circular image centering about the center of rotation of the optical lens. The image quality correcting means 90 further performs sharpening processing, smoothing processing and the like on the tomographic image to correct the image quality. The image quality correcting means 90 sends the tomographic image with image quality corrected to the display 24.

The timing at which the tomographic image is sent to the display 24 from the image quality correcting means 90 is not particularly limited. The tomographic image may be sent to the display 24 each time the processing of one line ends, with the tomographic image replaced and displayed on a per line basis, or the tomographic image may be sent to the display 24 at the stage where the processing of all lines ends, that is, the processing of all images acquired in one rotation of the optical lens 62 ends, and one circular tomographic image is formed.

The display 24, which may be a CRT device, a liquid crystal display device (LCD) or the like, displays the tomographic image sent from the image quality correcting means 90. The operation unit 36 comprises a regular input device, such as a keyboard or a mouse. Additionally, an operation screen may be displayed on the display 24 so as to function as the operation unit 36.

The control unit 32 controls each component of the optical tomographic imaging system 10, including the optical path length adjustor 18 and the optical path length switching unit 34. The processor 22, the display 24, and the operation unit 36 are connected to the control unit 32. The control unit 32 controls, for example, the operation of the optical path length switching unit 34 and the optical path length adjustor 18 based on operator instructions inputted from the inputting device of the operation unit 36. The control unit 32 performs operations such as inputting the processing conditions of the processor 22 and changing the display settings of the display 24.

Additionally, the control unit 32 receives the zero path position information sent from the optical path length switching unit 34 and supplies that zero path position information to the tomographic information generating means 84 of the processor 22.

Next, the behavior of the optical tomographic imaging system 10 will be described.

First, before measurement is started, the optical path imaging system 10 is set to the initial zero path position setting. The zero path position is set by the control unit 32 controlling the optical path length adjustor 18. The control unit 32 drives the mirror moving mechanism 72 so as to move the base 70 in the direction indicated by the arrow A and bring the object S into the measurable range, and adjusts the optical path length so that the zero path position is on the front side (the inside) of the object S, thereby setting the zero path position.

In the present embodiment, when the zero path initial setting is set, the optical path length switching unit 34 is set to a state in which the shorter optical path length is selected, for example. In this embodiment, the shorter optical path length is referred to as the first optical path length. This first optical path length corresponds to a zero path position (referred to as the first zero path position) set on the front side of the object S. The optical path length switching unit 34 sends information indicating that the first optical path length has been selected, that is, information indicating that the first zero path position on the front side has been set, as zero path position information to the control unit 32.

After the first zero path position is set, the optical probe 16 is inserted into the body to be inspected and measurement is started. First, the light source unit 12 emits the laser beam La. The emitted laser beam La is split by the splitting multiplexer 14 into the measuring light L1 and the reference light L2. The measuring light L1 is guided to the optical probe 16 and irradiated on the object S. The light obtained when the measuring light L1 is reflected at each depth position of the object S enters the optical probe 16 as the reflected light L3. This reflected light L3 is sent to the splitting multiplexer 14.

On the other hand, the reference light L2 enters the optical path length adjustor 18 via the optical path length switching unit 34. Then, the reference light L2 whose optical path length was adjusted by the optical path length adjustor 18 re-enters the splitting multiplexer 14 via the optical path length switching unit 34. The splitting multiplexer 14 multiplexes the reflected light L3 from the object S and the reference light L2 whose optical path length was adjusted by the optical path length adjustor 18 so as to generate the interference light L4 of the reflected light L3 and the reference light L2. The interference light is sent to the interference light detector 20 and detected as an interference signal.

The interference signal detected by the interference light detector 20 is sent to the processor 22 where it is subjected to processing for creating a tomographic image. The processor 22 first acquires the interference signal of line number n (where n is an arbitrary number) in the interference signal acquiring means 80, and converts the interference signal which is an analog signal thus acquired by the interference signal acquiring means 80 to a digital signal in the analog-to-digital converting means 82. Next, in the tomographic information generating means 84, the interference signal thus converted from analog to digital is subjected to FFT processing, and a tomographic image of line number n is acquired from the results of FFT processing.

At this time, the zero path position information has already been sent from the control unit 32 to the tomographic image generating means 84, and the tomographic image generating means 84 uses the resulting interference signals after FFT processing of either the inside or outside of the zero path position in accordance with that zero path position information. Here, the zero path position is set on the inside of the object S, and therefore the results of the direction facing the outside after FFT processing are used. With this arrangement, the range of a certain distance from the zero path position to the outside becomes the measurable range.

The tomographic image acquired in this manner is then sent to the image quality correcting means 90 and subjected to image processing for display, such as radial processing, sharpening processing, and the like. Subsequently, the tomographic image is sent to the display 24 and displayed.

Figure 5A:
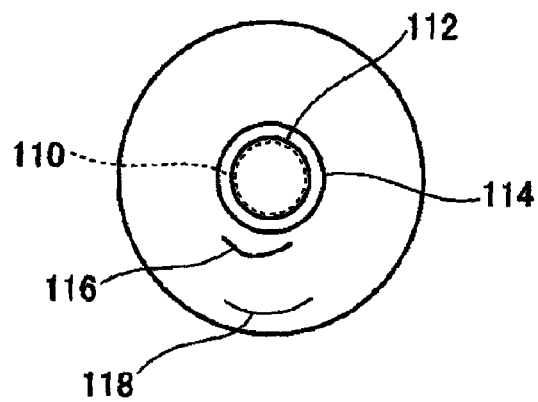
FIG. 5A and FIG. 5B are explanatory views of an example of a tomographic image acquired using the optical tomographic imaging system of FIG. 1.

FIG. 5A is a view schematically illustrating a tomographic image acquired in this manner. In FIG. 5A, the optical probe 16 is projected onto the center of the image. The circle denoted by reference numeral 112 is the inner surface of the probe sheath 52 of the optical probe 16, and the circle denoted by reference numeral 114 is the outer surface of the probe sheath 52 of the optical probe 16. A zero path 110 is set at a position that substantially matches the inner surface 112 of the probe sheath 52. Thus, the zero path 110 is set on the front side (inside) of the object S.

In the SS-OCT system employing a wavelength-swept light source, the range from the zero path to 10 mm, for example, is the measurable range. Note that, according to the knowledge of the inventors of the present invention, a high-resolution image is not necessarily obtained uniformly across the entire measurable range, but rather the resolution becomes higher as the distance to the zero path position decreases, and lower as the distance to the zero path position increases. This is conceivably because the interference signal becomes stronger (the interference intensity becomes higher) as the zero path position becomes closer, and the interference signal becomes weaker (the interference intensity becomes lower) as the zero path position becomes farther away, based on the characteristics of low coherence light.

In the example of FIG. 5A, the zero path 110 is set close to the inner surface 112 of the probe sheath 52, making it possible to obtain a high-resolution tomographic image of an object 116 located on the front side (inside) of the measurement range, i.e., in a region near the zero path 110. On the other hand, an object 118 located in a region on the back side (outside) of the measurement range is far from the zero path 110, resulting in a weak interference signal and a low-resolution tomographic image.

Thus, in a case where the region of the object 116 located on the front side of the measurement range is a region of interest, FIG. 5A obtained with the zero path 110 set on the inner edge of the measurement range is an effective image. Conversely, in a case where the region of the object 118 located on the back side of the measurement range is a region of interest, the optical path length switching unit 34 is switched, switching the zero path position to outside of the measurement range in order to obtain a high-resolution image of the region of interest.

The optical path length switching unit 34 is capable of performing switching during measurement as well. In a case where the operator observes a tomographic image displayed on the display 24 and assesses that a sufficient tomographic image has not been obtained since the region of interest is far from the zero path position, the operator inputs a zero path position switching instruction using the operation unit 36.

The instruction inputted from the operation unit 36 is sent to the control unit 32, and the control unit 32 performs control so as to switch optical path lengths in the optical path length switching unit 34. As a result, the optical path length switching unit 34 switches connection to a different optical path length, that is, to the longer optical path length (here, the second optical path length) in the present embodiment. This second optical path length corresponds to the edge of the back side of the measurable range and is a predetermined distance away from the first zero path position set on the front side in initial settings. Thus, when the optical path length switching unit 34 is switched to the second optical path length, the zero path position is switched to the second zero path position of the edge of the back side of the measurable range.

The control unit 32 switches the optical path length switching unit 34, and sends information indicating that the optical path length has been switched to the second optical path length, i.e., information indicating that the second zero path position on the back side has been set, as zero path position information to the tomographic information generating means 84 of the processor 22.

After the optical path length switching unit 34 is switched, the tomographic image is acquired using the same method as described above. At this time, the tomographic information generating means 84 of the processor 22 uses the zero path position information from the control unit 32, that is, the results after FFT processing of the direction facing the inside from the zero path position in accordance with the information indicating that the zero path is set on the outside. As a result, a tomographic image of the range of a certain distance from the zero path position to the inside is acquired.

Figure 5B:
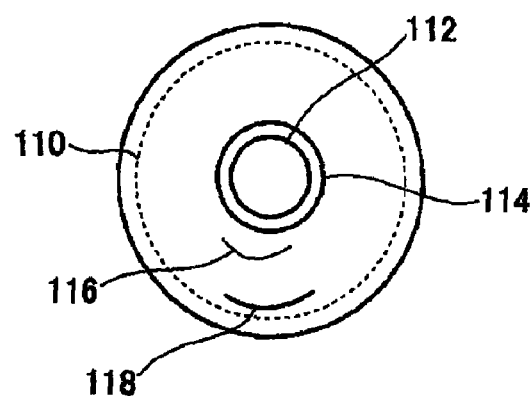

FIG. 5B is a view schematically illustrating a tomographic image acquired in this manner. In FIG. 5B, the zero path 110 is set near the edge of the back side (outside) of the measurement range, bringing the region outside the center of the measurement range closer in distance to the zero path 110, making it possible to obtain a high-resolution tomographic image. Thus, the object 118 located in the region on the outside of the measurement range is displayed in high resolution.

Here, in a case where the zero path 110 is set on the outside of the measurable range, the interference light needs to reach deep into the object, causing the interference light to dampen. Yet, due to the proximity to the zero path position, the S/N ratio increases, making it possible to obtain a high-resolution tomographic image.

On the other hand, the region located on the front side (inside) of the center of the measurement range is far from the zero path 110, resulting in a weak interference signal and a low-resolution tomographic image. Thus, the object 116 located in the region on the inside of the measurement range is displayed at low resolution.

In this manner, according to the optical tomographic imaging system 10 of the present invention, the zero path position can be switched between the front side (inside) and back side (outside) of the measurement range even during measurement, making it possible to easily switch the region in the depth direction within the measurement range where it is possible to obtain a high-resolution image, thereby making it possible to obtain a high-resolution image of the region of interest.

While the initial position of the zero path position was set to the front side (inside) of the measurement range and then arbitrarily switched to a position at the back side of the measurement range in the above, the initial position of the zero path position may be set to the back side (outside) of the measurement range.

Figure 6:
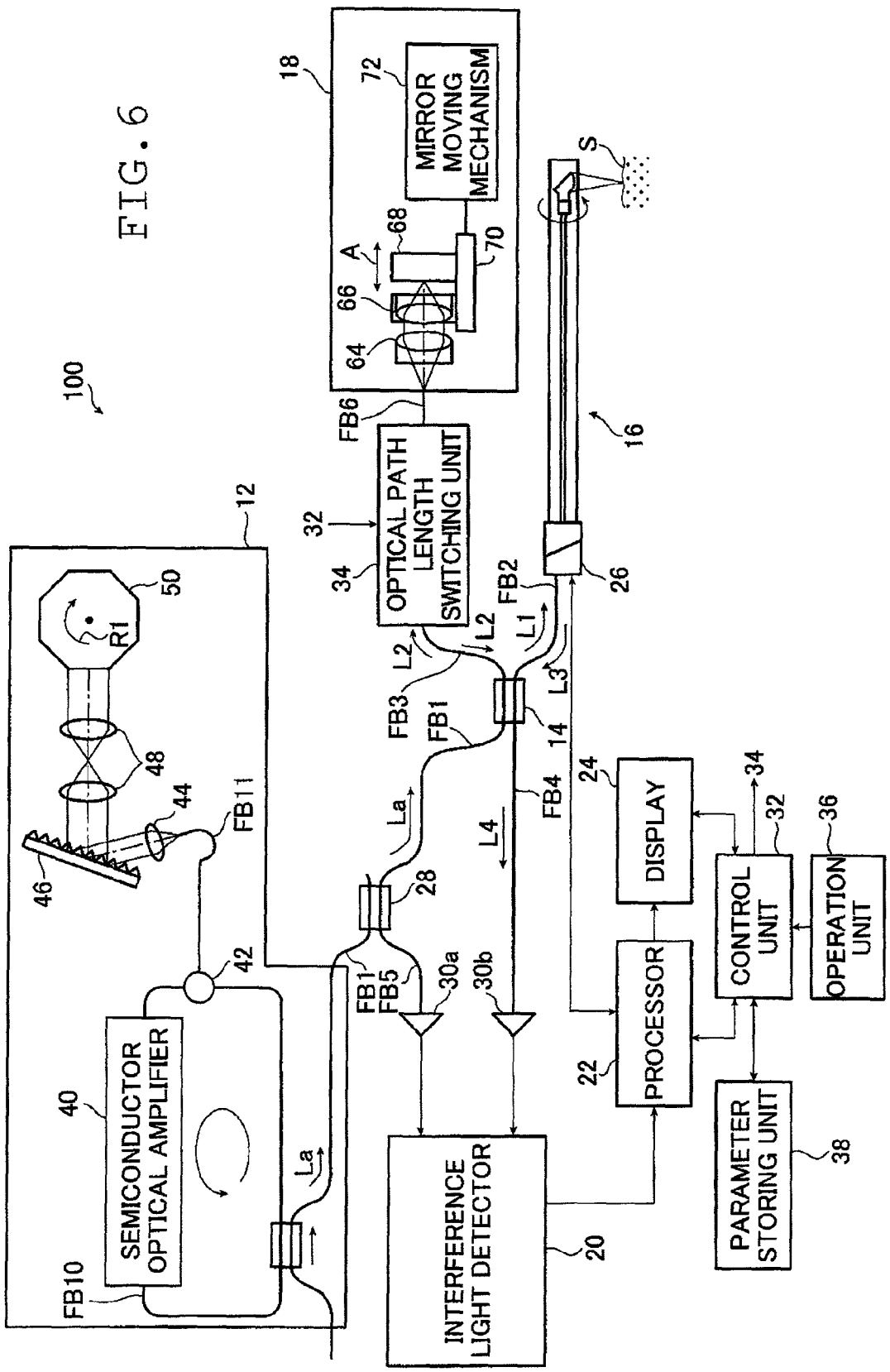
FIG. 6 is a block diagram schematically illustrating the configuration of another embodiment of an optical tomographic imaging system according to the present invention.

Next, the second embodiment of the present invention will be described. FIG. 6 is a block diagram schematically illustrating the general configuration of the second embodiment of an optical tomographic imaging system according to the first aspect of the present invention. An optical tomographic imaging system 100 shown in FIG. 6 is the same as the optical tomographic imaging system 10 of FIG. 1, but further comprises a parameter storing unit 38. Note that all other elements or constituents have basically the same configuration as those of the optical tomographic imaging system 10, equivalent elements or constituents are denoted using the same reference numerals, and the detailed descriptions thereof will be omitted. The following mainly describes how the optical tomographic imaging system 100 differs from the optical tomographic imaging system 10.

The optical tomographic imaging system 100 is provided with the parameter storing unit 38 that is connected to the control unit 32. The parameter storing unit 38 stores the position parameters of the zero path corresponding to the measurement area and the region of interest.

In a case where the optical tomographic imaging system 100 is used as a medial system and there are different areas (objects S) to be measured by the optical probe 16, such as the esophagus and the stomach, the depth from the surface of the main region of interest differs according to the area to be measured. Additionally, the depth of the region of interest also differs within the same measurement area, according to factors such as the purpose of measurement and symptoms.

As described above, the OCT system configured to acquire information on the tomographic image by coherence light is capable of acquiring a higher resolution image closer to the zero path position, and the image quality deteriorates as the distance from the zero path position increases. Thus, the preferred value of the zero path position for acquiring a high-resolution image of the region of interest differs according to the measurement area and the region of interest.

Normally, since the zero path position (the first zero path position) on the front side of the measurement range is a highly reliable position initially set on the inner surface of the probe sheath 52 of the optical probe 16, the zero path position to which the position is switched per measurement area is preferably a second zero path position on the back side (outside) of the measurement range.

Based on the above, the optical tomographic imaging system 100 presets the position parameters of the second zero path position in accordance with the respective measurement areas, and stores these parameters in the parameter storing unit 38. Furthermore, the zero path position parameters corresponding to the depth range of the region of interest are preferably stored in the parameter storing unit 38 for the respective measurement areas.

A plurality of optical paths with optical path lengths corresponding to the zero path position parameters are prepared in the optical path length switching unit 34, making it possible to switch the optical path length in accordance with the parameters. Or, the optical path length switching unit 34 comprises a configuration that makes it possible to arbitrarily switch the optical path length in accordance with the zero path position parameters.

In a case where the configuration makes it possible for the optical path length switching unit 34 to arbitrarily change the optical path length, the parameters stored in the parameter storing unit 38 may be freely set by the operator. Additionally, the switching positions of the second zero path position may be simply prepared in stages and the parameters corresponding to each position may be stored in the parameter storing unit 38 so that the second zero path position is switched when the operator selects the range of depth of the region of interest.

Figure 7:
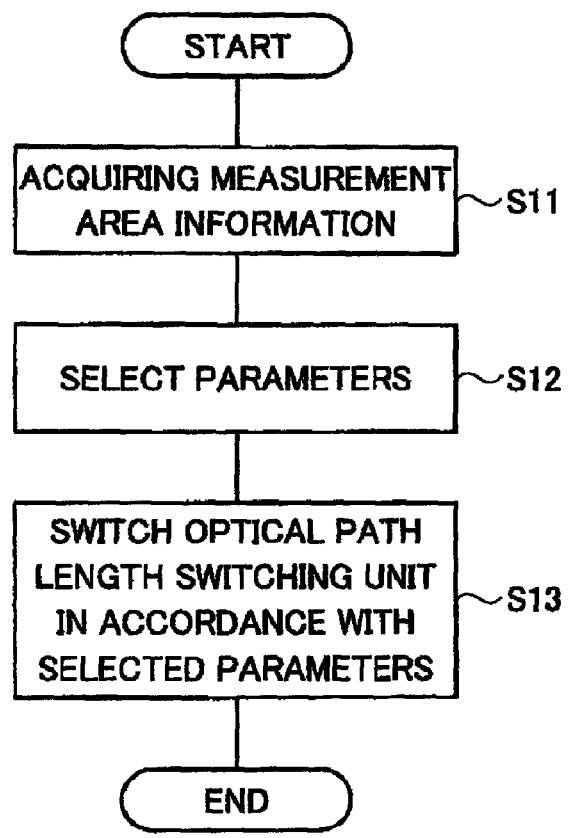
FIG. 7 is a flowchart illustrating an example of a method of switching the zero path position by the optical path length switching unit of FIG. 3.

The setting method of the second zero path position of the optical tomographic imaging system 100 will now be described with reference to FIG. 7. When there is an instruction input from the operation unit 36 by the operator at the start of measurement or during measurement, the control unit 32 acquires the inputted measurement area information or depth information of the region of interest (step S11) and, based on the acquired measurement area information, selects and reads the parameters corresponding to the measurement area information from the parameter storing unit 38 (step S12).

Next, the control unit 32 switches the optical path length switching unit 34 in accordance with the parameters read from the parameter storing unit 38, thereby switching the optical path length of the reference light L2 (step S13). Switching the optical path length of the reference light L2 switches the zero path position.

In addition to switching the optical path length switching unit 34 in step S13, the control unit 32 also supplies the zero path information corresponding to the parameters read from the parameter storing unit 38 to the processor 22. The tomographic information generating means 84 of the processor then processes the interference signal corresponding to the zero path position information supplied from the processor 22, thereby generating the tomographic information of the appropriate region.

Thus the parameters are maintained according to the measurement area and the region of interest, making it possible to easily switch the zero path position according to the measurement area and region of interest. Additionally, the zero path position can be easily switched even in a case where the measurement area and region of interest are changed during measurement, making it possible to perform measurements more quickly and further improve the user-friendliness of the optical tomographic imaging system.

Next, the third embodiment of the present invention will be described.

In the aforementioned first embodiment and second embodiment, a tomographic image acquired by setting the zero path position to the front side (inside) and a tomographic image acquired by setting the zero path position to the back side (outside) in accordance with the region of interest were respectively obtained. The images obtained in this manner exhibited a higher resolution in a region close to the zero path position, and a lower resolution in a region far from the zero path position, as described with reference to FIG. 5A and FIG. 5B.

Conversely, in the present embodiment, a tomographic image acquired by setting the zero path position to the front side (inside) is synthesized with a tomographic image acquired by setting the zero path position to the back side (outside) so as to obtain a high-resolution tomographic image at large.

Figure 8:
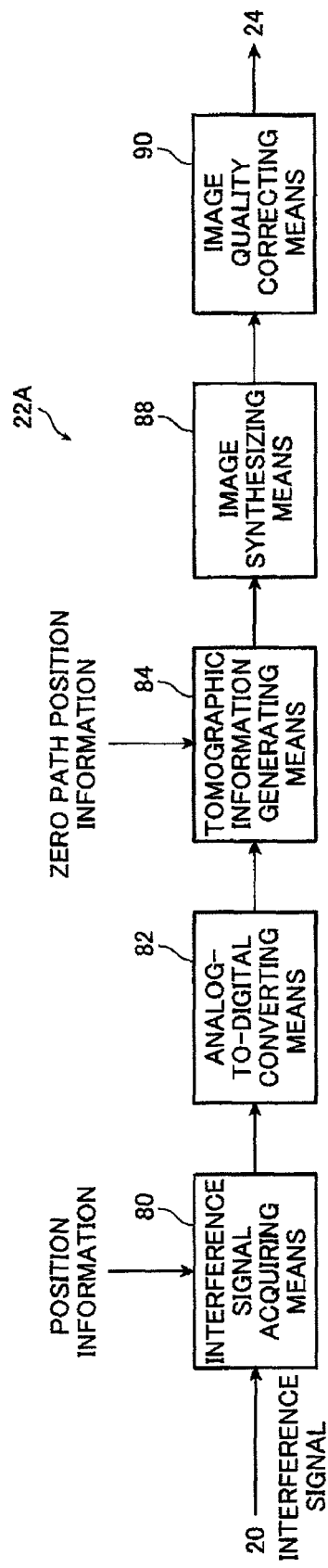
FIG. 8 is a block diagram schematically illustrating the configuration of an embodiment of the processor of the third embodiment of the present invention.
Figure 9:
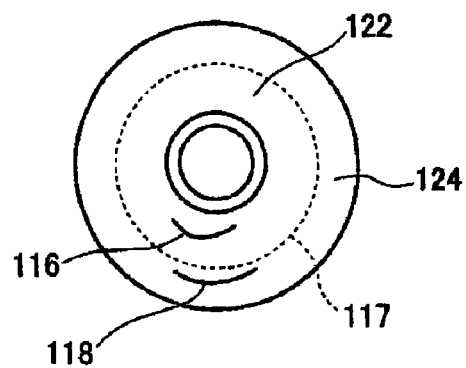
FIG. 9 is an explanatory view of an example of a tomographic image synthesized by the image synthesizing means of the processor of FIG. 8.

FIG. 8 is a block diagram schematically illustrating the configuration of a processor 22A of an optical tomographic imaging system of the present embodiment. The processor 22A shown in FIG. 8 differs from the processor 22 (refer to FIG. 4) of the aforementioned examples in that the processor 22A further comprises image synthesizing means 88 between the tomographic information generating means 84 and the image quality correcting means 90. In this embodiment, other than the configuration of the processor 22A, the configuration is the same as the configuration of the optical tomographic imaging system 10 of the aforementioned first embodiment, and the optical tomographic imaging system 100 of the aforementioned second embodiment. The present embodiment will now be described with reference to the optical tomographic imaging system 10 of FIG. 1.

In the optical tomographic imaging system 10 of the present embodiment, first the optical path length adjustor 18 sets the zero path position to the initial setting with the optical path length switching unit 34 switched to the first optical path length. As a result, the first zero path position is set to the inner surface of the probe sheath 52 of the optical probe 16, which is the initial setting value. This position is established as the inner most position of the measurement range. Next, the control unit 32 switches the optical path length switching unit 34 to the second optical path length based on instruction input from the operation unit 36, thereby switching the zero path position to the second zero path position.

The control unit 32 turns the optical lens 62 (refer to FIG. 2) of the optical probe 16 using the rotary drive unit 26, and measures the object S while switching the zero path position between the inside and the outside of the measurement range using the optical path length switching unit 34, in synchronization with that rotational scanning period. For example, the zero path position is switched between the first zero path position on the inside of the measurement range and the second zero path position on the outside of the measurement range on a per rotation basis of the optical lens 62.

In a case where the system performs flatbed scanning with the measuring light L1, the optical tomographic imaging system 10 may be synchronized with the flatbed scanning period of the optical lens to switch the zero path position and perform measurement.

The processor 22A receives the interference signal detected from the interference light L4 based on the reflected light L3 acquired by the optical probe 16, and the interference signal acquiring means 80 correlates the interference signal and the position information on the measuring position. The interference signal correlated with the position information on the measuring position is converted to a digital signal by the analog-to-digital converting means 82, and then sent to the tomographic information generating means 84.

The tomographic information generating means 84 separates the interference signals into the interference signal acquired at the first zero path position and the interference signal acquired at the second zero path position based on the information at the time the zero path is switched by the optical path length switching unit 34, respectively performs FFT processing on the selected interference signals based on the corresponding zero path position information, and acquires two tomographic images. That is, the interference signal acquired at the first zero path position is subjected to FFT processing and the result in the direction facing the back side is used to generate tomographic image information, and the interference signal acquired at the second zero path position is subjected to FFT processing and the result in the direction facing the front side is used to generate tomographic image information. As a result, two images of the same object S, a tomographic image with the front side (inside) of the measurement range at a high-resolution and a tomographic image with the back side (outside) of the measurement range at a high-resolution are acquired.

Next, the image synthesizing means 88 synthesizes the two tomographic images obtained by the tomographic information generating means 84 so as to generate a single synthesized image. Since the time at which each of the two tomographic images was acquired differs slightly, a small amount variation is believed to exist between the two images. For this reason, the scales of both images are preferably aligned so as to correct this variation before the images are synthesized. The scales of the two images can be aligned by calculating the distance between the outer surface of the probe sheath 52 and the equivalent position on the front surface of the object S for the image of the first zero path position and the image of the second zero path position, respectively, and matching the values to either value.

The image synthesizing method performed by the image synthesizing means 88 may be, for example, a method wherein a high-resolution tomographic image 122 which includes half of the measurement range from the zero path position of the image obtained at the first zero path position, i.e., the inside half of the image, and a high-resolution tomographic image 124 which includes half of the measurement range from the zero path position of the image obtained at the second zero path position, i.e., the outside half of the image, are combined at a borderline 117 of the image usage region so as to obtain an overall high-resolution tomographic image.

The width of the image usage region of each image is preferably arbitrarily variable in the area from the zero path position of the image to the edge on the side opposite the measurement range. For example, the width of the usage region of each image may be set and changed based on input from the operation unit 36. With this arrangement, the image usage region can be set to arbitrary ratios so that, for example, each ratio is 50% (half) in the radial direction or 70% for the inside and 30% for the outside.

The borderline region of the image usage region may be given a width so as to weight and connect both images of the borderline region. Additionally, for one or both images, the entire measurement range may be set as the image usage region, i.e., the entire image acquired may be used, weighted, and synthesized. These conditions as well may be arbitrarily or selectively set using the operation unit 36.

The tomographic image thus synthesized by the image synthesizing means 88 is subjected to image quality correction by the image quality correcting means 90, and displayed on the display 24.

According to the above third embodiment, it is possible to switch the zero path position to the front side (inside) and back side (outside) so as to obtain two tomographic images, combine the respective high-resolution sections of these tomographic images to obtain a single high-resolution tomographic image at large and display that image on the display 24, thereby making it possible to directly and instantly check the high-resolution image of both the object 116 and the object 118, which are regions of interest differing in depth.

Next, the fourth embodiment of the present invention will be described.

In this embodiment, the optical tomographic imaging system of the present invention capable of switching the zero path position between the inside and the outside of the measurement region automatically switches the zero path position to the first zero path position located on the inside when the optical probe 16 is far away from the object S, thereby making the area near the surface of the object S easy to view.

Figure 10:
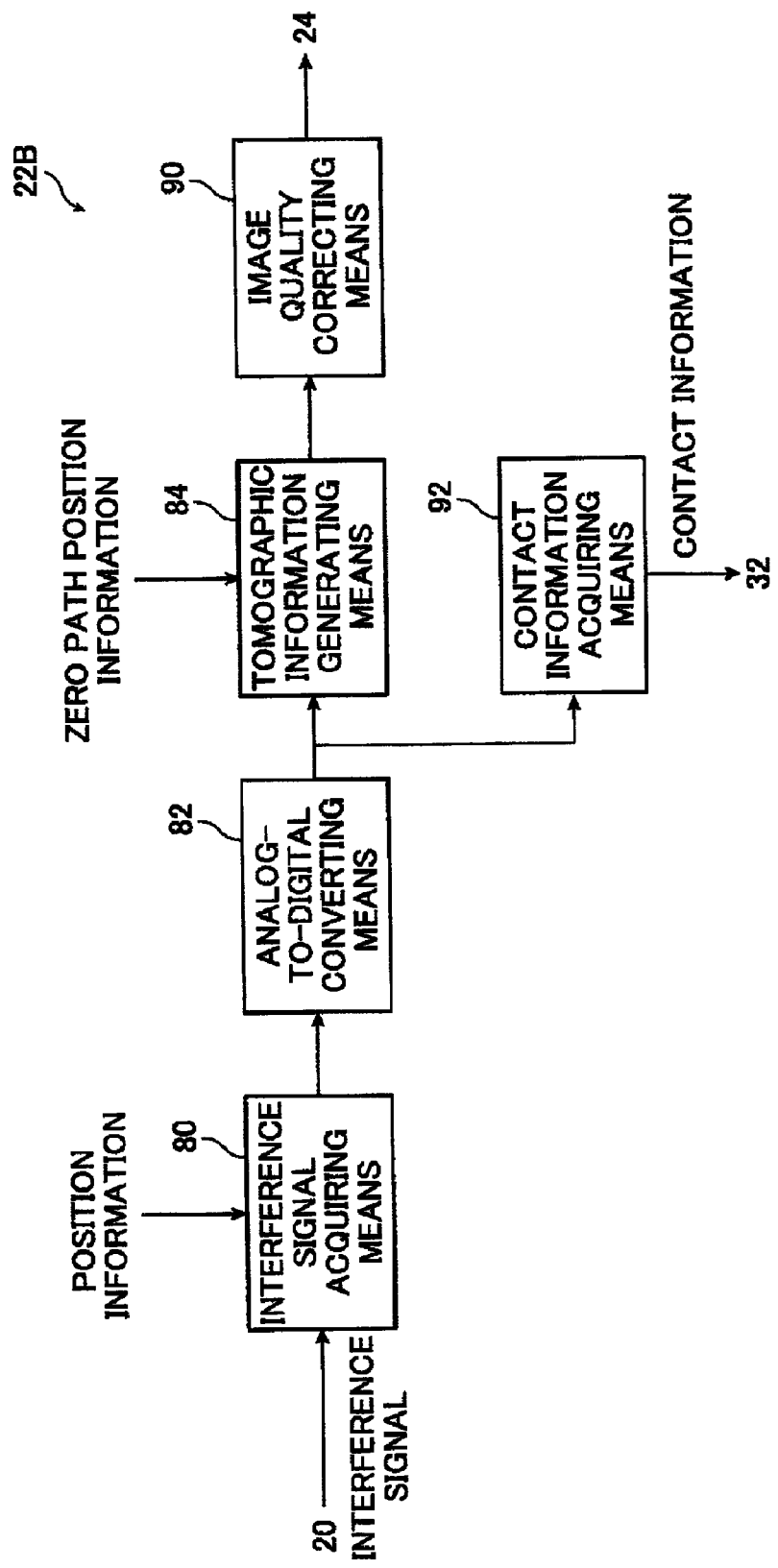
FIG. 10 is a block diagram schematically illustrating the configuration of an embodiment of the processor of the fourth embodiment of the present invention.

FIG. 10 is a block diagram schematically illustrating the configuration of a processor 22B of the optical tomographic imaging system of the present embodiment. The processor 22B shown in FIG. 10 differs from the processor 22 (refer to FIG. 4) of the aforementioned first embodiment and second embodiment in that the processor 22B further comprises contact information acquiring means 92 downstream from the analog-to-digital converting means 82. In this embodiment, the configuration of elements and constituents other than the processor 22A is the same as that of the optical tomographic imaging system 10 of the aforementioned first embodiment or the optical tomographic imaging system 100 of the aforementioned second embodiment.

The contact information acquiring means 92 detects the positional relationship of the optical probe 16 and the object S, i.e., detects the distance between the two, acquires information indicating whether or not the optical probe 16 is contacting the object S (contact information), and outputs that contact information to the control unit 32.

The control unit 32, upon receipt of the contact information from the contact information acquiring means 92, controls the optical path length switching unit 34 in accordance with that information. That is, the control unit 32 controls the optical path length switching unit 34 so that the zero path position is automatically switched to the first zero path position located on the inner edge of the measurement range in a case where the optical probe 16 is far away from the object S. Furthermore, as described above, the first zero path position is set to the inner surface of the probe sheath 52 of the optical probe 16.

Thus, when the optical probe 16 is separated from the object S by a certain distance or greater, the zero path position is switched to the first zero path position, thereby increasing the resolution of the surface of the object S. With this arrangement, the overall shape of the object S becomes easier to grasp, thereby improving ease in measurement.

The method used by the contact information acquiring means 92 to acquire contact information will now be described.

The contact information acquiring means 92 uses the interference signal converted to a digital signal by the analog-to-digital converting means 82, and detects the position of the outer surface of the probe sheath 52 at a position though which the measuring light L1 passes and the position of the surface of the object S that is closest to the probe sheath 52, thereby detecting the contact state of the probe sheath 52 and the object S from these distances.

The position of the outer surface of the probe sheath 52 is detected as follows.

First, information on the relationship between depth direction and interference intensity is acquired by replacing the frequency component provided in the information on the relationship between frequency component and interference intensity, which was acquired upon performing FFT processing on the interference signals of an arbitrary line, with information indicating the depth direction (the direction away from the rotational center).

Figure 12:
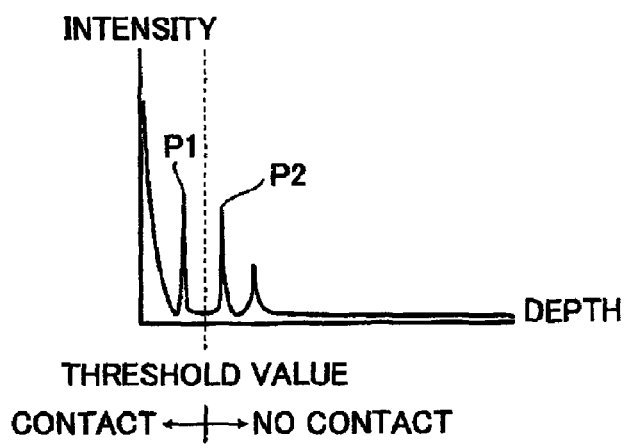
FIG. 12 is a graph schematically showing an example of calculation results acquired by performing FFT processing on an interference signal.

FIG. 12 is a graph illustrating an example of the calculation results (relationship between depth direction position and interference intensity) acquired upon performing FFT processing on the interference signals. In FIG. 12, the horizontal axis indicates depth direction, and the vertical axis indicates intensity. In FIG. 12, the depth at which the intensity peak is detected indicates the position where properties change.

With the optical tomographic imaging system 10, the material on which the measuring light L1 emitted from the optical lens 62 of the optical probe 16 is first reflected is the probe sheath 52. Thus, the first peak position P1 of FIG. 12 indicates the position of the outer surface of the probe sheath 52. Here, the optical lens 62 and the probe sheath 52 of the optical probe 16 are disposed on the same axis. Thus, the distance between the optical axis of the optical lens 62 and the outer peripheral surface of the probe sheath 52 is constant regardless of the measuring position, making it possible to use a position on the outer peripheral surface of the probe sheath 52 detected on one line for all measuring positions.

Furthermore, FIG. 12 shows the results based on the interference signal when the object S was measured. Normally, however, the interference signal when the object S is not measured is used for measuring a position on the outer surface of the probe sheath 52. In such a case, the peak of a position that is deeper than the peak P1 will not show up in FIG. 12.

Next, detection of the contact state of the probe sheath 52 and the object S will be described.

First, similar to detection of the position of the outer peripheral surface of the probe sheath 52 described above, FFT processing is performed on the interference signals of one line, and information on the depth direction and interference intensity is acquired. As a result, a graph such as that shown in FIG. 12 is obtained.

In FIG. 12, a plurality of peaks in the depth direction are detected. Of the plurality of peaks, the first peak P1, as described above, indicates the outer peripheral surface of the probe sheath 52, and the peak P2 following the peak P1 indicates the surface of the object S.

Based on this result, the contact information acquiring means 92 detects the distance between the outer surface of the probe sheath 52 and the surface of the object S and, from the detected distance, detects the contact state of the probe sheath 52 and the object S. That is, the contact information acquiring means 92 assesses that the probe sheath 52 and the object S are in a state of contact in a case where the distance between the probe sheath 52 and the object S is less than or equal to a threshold value, and assesses that the probe sheath 52 and the object S are in a state of no contact in a case where the detected distance is greater than the threshold value.

For the neighboring line as well, the contact information acquiring means 92 similarly assesses the contact state of the probe sheath 52 and the object S. The contact information acquiring means 92 thus assesses the contact state in the entire measurement region, that is, the entire periphery of the probe sheath 52, on a per line basis. Next, the contact information acquiring means 92 detects whether or not a contact region between the probe sheath 52 and the object S exists based on the assessment results of the contact state of the entire periphery of the object S and the probe outer periphery, and outputs the detection result as contact information to the control unit 32.

Next, another example of the fourth embodiment of the present invention will be described.

While the zero path position was switched to the front side (inside) in the aforementioned example, the control unit 32 may adjust the optical path length switching unit 34 so that the zero path position aligns with the surface of the object S that is nearest based on the contact information from the contact information acquiring means 92. In such a case, in addition to information on whether or not a contact region between the probe sheath 52 and the object S exists, information on the position (depth) of the object S is also outputted as contact information from the contact information acquiring means 92 to the control unit 32. Additionally, the optical path length switching unit 34 comprises a configuration that makes it possible to set the first zero path position to any position.

In a case where the probe sheath 52 and the object S are detected as in a state of no contact, the zero path position is aligned to the position of the peak P2 of the line where the probe sheath 52 and the object S are closest to each other, thereby making it possible to measure the area near the surface of the object S at an even higher resolution.

In such a case, the contact information acquiring means 92 of the processor 22 outputs information on the position of the surface of the object S of the line number where the probe sheath 52 and the object S are closest to each other in the entire measurement region (the entire periphery of the optical probe 16), i.e., information on the position of the peak P2, as contact information to the control unit 32.

The control unit 32, based on the received information on the position of the peak P2, calculates the amount of movement (the amount of shift) of the zero path position from the present zero path position (first zero path position) set to the inner peripheral surface of the probe sheath 52 and, based on the result, switches the optical path lengths set in with the optical path length switching unit 34. Once the zero path position is set to the surface of the object S in this manner, the optical probe 16 performs rotational scanning so as to obtain the interference signal.

Figure 11:
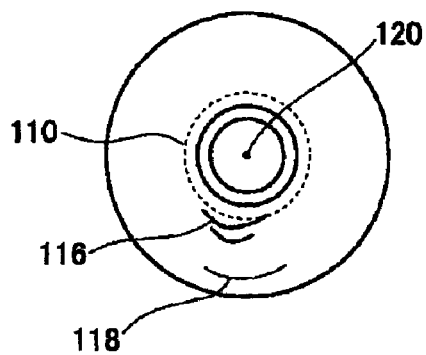
FIG. 11 is an explanatory view illustrating a display example of a tomographic image.

Here, the processor 22 generates the tomographic image from the acquired interference signal. However, since the zero path position has been moved (shifted) from the position where the zero path position on the front side (inside) was set as the initial position, the tomographic image cannot be generated as usual as is. That is, given that the first zero path position matches the inner surface of the probe sheath 52, the tomographic information generating means 84 adds to each line the distance from the center of the probe sheath 52 to the inner surface as an offset value, thereby generating a circular image centering about the axis of the probe sheath 52, as shown in FIG. 5 and FIG. 11. However, the first zero path position after movement is further moved a distance equal to the predetermined amount of movement from the center of the probe sheath 52. In other words, the first zero path position after movement is moved a distance equal to the predetermined amount of movement from the original first zero path position, i.e., from the inner surface of the probe sheath 52. As a result, the image based on the interference signal after the first zero path position is moved shows a state that differs from the actual positional relationship between the probe sheath 52 and the object S when the original processing settings are left as is.

Here, when generating the tomographic image, the tomographic information generating means 84 of the processor 22 calculates the amount of movement of the zero path position and the distance to the center of the original image, and performs operations so as to achieve an actual circular display centering about the probe sheath 52. That is, the image is offset in the depth direction (or optical axial direction) by an amount equivalent to the amount by which the zero path position was moved.

In this manner, in a case where the object S and the probe outer periphery are in a state of no contact, the zero path position is set to the surface of the object S, making it possible to measure the area near the surface of the object S at a higher resolution.

While in the above example the first zero path position is moved by adjusting the optical path length in the optical path length switching unit 34, the first zero path position may be moved by adjusting the optical path length adjustor 18.

Further, while the above described is an optical tomographic imaging system that performs rotational scanning with the measuring light, the optical tomographic imaging system of the present invention may also be applied to a system that generates an optical tomographic image of an object by performing flatbed scanning using the measuring light.

Further, while the above described is an embodiment wherein the zero path position is switched by switching the optical path length of the reference light L2 as a preferred embodiment, the optical path length of the measuring light L1 may be switched to switch the zero path position.

The optical tomographic imaging system of the first aspect and the tomographic image acquiring method of the second aspect of the present invention are basically configured as described above.

Next, the optical tomographic image forming method of the third aspect and the optical tomographic imaging system of the fourth aspect of the present invention will be described with reference to FIG. 1 to FIG. 3C, FIG. 6, and FIG. 13 to FIG. 22.

First, the fifth embodiment of the optical tomographic imaging system of the fourth aspect of the present invention will be described.

FIG. 1 to FIG. 3C previously used to describe the optical tomographic imaging system of the first aspect of the present invention which implements the tomographic image acquiring method of the second aspect of the present invention may be similarly used when describing the optical tomographic imaging system of the fourth aspect of the present invention, which implements the optical tomographic image forming method according to the third aspect of the present invention. That is, FIG. 1 is a block diagram schematically illustrating the configuration of the fifth embodiment of the optical tomographic imaging system of the fourth aspect of the present invention, which implements the optical tomographic image forming method of the third aspect of the present invention. The optical tomographic imaging system 10 shown in FIG. 1 is a so-called Swept Source OCT (SS-OCT) that uses a wavelength-swept light source to scan an object with measuring light and obtain a reflected light so as to obtain a tomographic image in the optical axial direction of the measuring light based on the reflected light, reference light, and interference light.

In the SS-OCT system employing a wavelength-swept light source, the range from the zero path to 10 mm, for example, is the measurable range. Note that, according to the knowledge of the inventors of the present invention, a high-resolution image is not necessarily obtained uniformly across the entire measurable range, but rather the resolution becomes higher as the distance to the zero path position decreases, and lower as the distance to the zero path position increases. This is conceivably because the interference signal becomes stronger (the interference intensity becomes higher) as the distance to the zero path position decreases, and the interference signal becomes weaker (the interference intensity becomes lower) as the distance to the zero path position increases, based on the characteristics of low coherence light.

Accordingly, the present invention is characterized by the fact that a plurality of zero path positions are set within the measurement range and, when the same object is measured, the zero path position is switched a plurality of times so as to obtain a synthesized image that combines the sections of high-resolution of the tomographic images acquired at each zero path position. With this arrangement, the present invention makes it possible to obtain a high-resolution tomographic image across the entire measurement range.

The configuration of the fifth embodiment of the optical tomographic imaging system of the fourth aspect of the present invention and the configuration of the first embodiment of the optical tomographic imaging system of the first aspect of the present invention are identical except the configuration of the function of the optical path length switching unit 34 and the configuration of the processor 22 of the optical tomographic imaging system 10 shown in FIG. 1. The configuration of the optical tomographic imaging system 10 applied to the present embodiment was previously described in the first embodiment with reference to FIG. 1 and FIG. 2, and therefore a description thereof will be omitted.

Here, the optical path length switching unit 34 of the optical tomographic imaging system 10 of the present embodiment is disposed between the splitting multiplexer 14 and the optical path length adjusting unit 18, the splitting multiplexer 14 and the optical path length switching unit 34 are connected by the optical fiber FB3, and the optical path length switching unit 34 and the optical path length adjusting unit 18 are connected by the optical fiber FB6.

In the present embodiment, the optical path length switching unit 34 comprises a configuration that makes it possible to switch to a plurality of preset optical path lengths, and the optical path length is selectively switched based on the control from the control unit 32. The optical path length switching unit 34 has a reference optical path length to which the initial position (first reference position) of the zero path is set, and a plurality of optical path lengths that differ in length with respect to the reference optical path length in stages.

The maximum difference between the optical path lengths of the optical path length switching unit 34 is set so that the value is substantially equal to or greater than the difference between the maximum value and the minimum value of the depth of the measurable range of the optical tomographic imaging system 10. Thus, the optical path length switching unit 34 switches the optical path in a plurality of stages within the range from the minimum optical path length to the maximum optimum path length, making it possible to detect a signal based on the reflected light at a plurality of positions (depths) across the entire range from the inner edge to the outer edge of the measurable range of the optical tomographic imaging system 10.

In the present embodiment, the reference optical path length is set as the minimum optical path length, and four optical path lengths that vary from the reference optical path length in four stages are set. The optical path length switching method and behavior will be described later.

Note that the specific configuration of the optical path length switching unit 34 is not particularly limited as long as the optical path length can be switched to predetermined optical path lengths. For example, a configuration such as that shown in FIG. 3A to FIG. 3C may be used for the optical path length switching unit 34 as previously described in the first embodiment. The specific configuration of the optical path length switching unit 34 was previously described in the first embodiment, and a description thereof will therefore be omitted.

Figure 13:
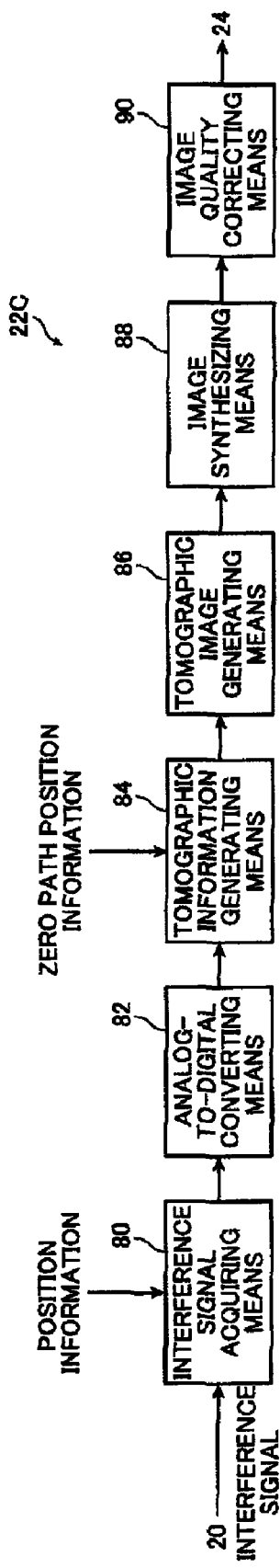
FIG. 13 is a block diagram schematically illustrating the configuration of an embodiment of the processor of the fifth embodiment of the present invention.

FIG. 13 schematically illustrates the configuration of a processor 22C of the present embodiment that is applicable in place of the processor 22 of the optical tomographic imaging system 10 shown in FIG. 1. The processor 22C shown in this figure acquires a tomographic image from the interference signal detected by the interference light detector 20. As shown in FIG. 13, the processor 22C comprises the interference signal acquiring means 80, the analog-to-digital converting means 82, the tomographic information generating means 84, a tomographic image generating means 86, the image synthesizing means 88, and the image quality correcting means 90.

The processor 22C shown in FIG. 13, except further comprising the tomographic image generating means 86 and the image synthesizing means 88, has the same configuration as the processor 22 shown in FIG. 4. Equivalent elements and constituents are therefore denoted using the same reference numerals, and descriptions thereof will be omitted. The main differences will now be described.

In the processor 22C shown in FIG. 13, the interference signal acquiring means 80 correlates the received interference signal with the position information on the measuring position, the analog-to-digital converting means 82 converts the interference signal correlated with the position information on the measuring position to a digital signal, and the tomographic information generating means 84 generates a tomographic image of each measuring position and sends the generated tomographic image to the tomographic image generating means 86.

In a case where the tomographic image generated by the tomographic information generating means 84 includes a virtual image, the tomographic image generating means 86 identifies and removes that virtual image, correcting the image to a tomographic image showing a real image. The correction method will be described in detail later.

The tomographic image generating means 86 performs logarithmic conversion and radial conversion of the tomographic image at each measuring position that was generated by the tomographic information generating means 84 to dispose the tomographic image in line number sequence and obtain a circular image centering about the center of rotation of the optical lens. The tomographic image generating means 86 generates a plurality of tomographic images corresponding to the number of zero path positions.

The image synthesizing means 88 synthesizes the plurality of tomographic images obtained by the tomographic image generating means 86 so as to generate a single synthesized image.

Examples of the image synthesizing method used by the image synthesizing means 88 include a method wherein a circular area within each image obtained at each zero path position, from that zero path position to the next zero path position on the side established as the object, is established as an image usage region, and each image usage region of a plurality of images with differing zero path positions is extracted and synthesized. For example, when the measurement range is divided into n equal sections and the zero path position is switched to n zero path positions to obtain n images, the range of 1/n of the measurement range from each zero path position is established as an image usage region. By establishing the region near the zero path position as the image usage region and generating a synthesized image in this manner, the present invention makes it possible to obtain a high-resolution tomographic image of the entire area.

Figure 15A:
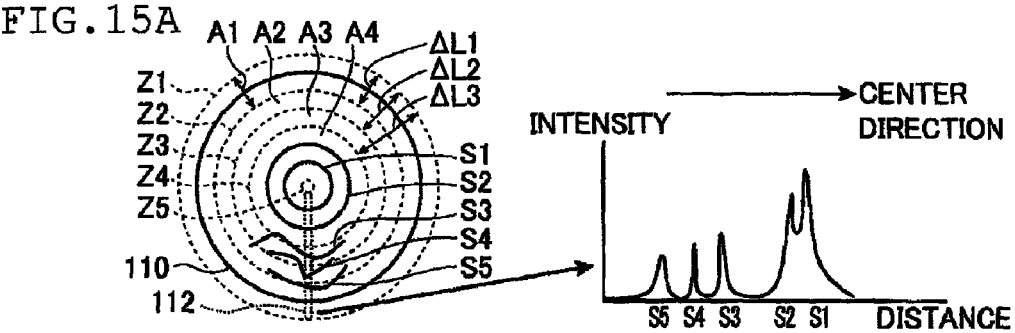
FIG. 15A to FIG. 15E are explanatory views illustrating a display example of a tomographic image at each zero path position and a graph schematically illustrating an example of the calculation results acquired by performing FFT processing on the interference signal of the fifth embodiment of the present invention.

As will be described later, FIG. 15A is a schematic view illustrating a tomographic image acquired at a zero path position Z1 (a position on the outside the measurement range). In this figure, Z1 to Z5 indicate switched zero path positions, and A1 to A4 indicate the image usage regions of the images acquired at zero path positions Z1 to Z4. In this example, the image synthesizing means 88 generates a synthesized image by combining the image area A1 of the image obtained at the backmost (outermost) zero path position Z1, the image area A2 of the image obtained at the zero path position Z2 located one position farther forward (inward) than Z1, the image area A3 of the image obtained at the zero path position Z3 located one position farther forward (inward) than Z2, and image area A4 of the image obtained at the zero path position Z4 located one position farther forward (inward) than Z3, at zero path positions Z2 to Z4.

The width of the image usage region of each image may be set as a fixed value, or may be automatically calculated by the image synthesizing means 88 in accordance with the measurement range (image range) and number of divisions (number of images) to be set. Additionally, the width of the image usage region is preferably arbitrarily variable in the area from the zero path position of that image to the edge on the side opposite the measurement range. For example, the width of the usage region of each image may be set and changed based on input from the operation unit 36.

The borderline region of the image usage region may be given a width so as to weight and connect both images of the borderline region. Additionally, for example, the entire front side (inside) region from the zero path position of each image obtained at the zero path position of the back side (outside) may be established as the image usage region, that is, the entire region of the side established as the object of the acquired image may be used, weighted, and synthesized. These conditions as well may be arbitrarily or selectively set using the operation unit 36.

The time at which each of the plurality of tomographic images was acquired differs slightly. As a result, a small amount of variation is believed to exist between each image. Accordingly, the image synthesizing means 88 preferably aligns the scale of each image so as to correct this variation before synthesizing the images.

The tomographic images synthesized into a single synthesized image by the image synthesizing means 88 are subjected to image quality correction by the image quality correcting means 90, and then displayed on the display 24.

Note that, in the present embodiment, the control unit 32 acquires the zero path position information to which the optical path length switching unit 34 is set, and supplies that zero path position information to the tomographic information generating means 84 of the processor 22C.

Next, the behavior of the optical tomographic imaging system 10 of the present embodiment will be described.

Figure 14:
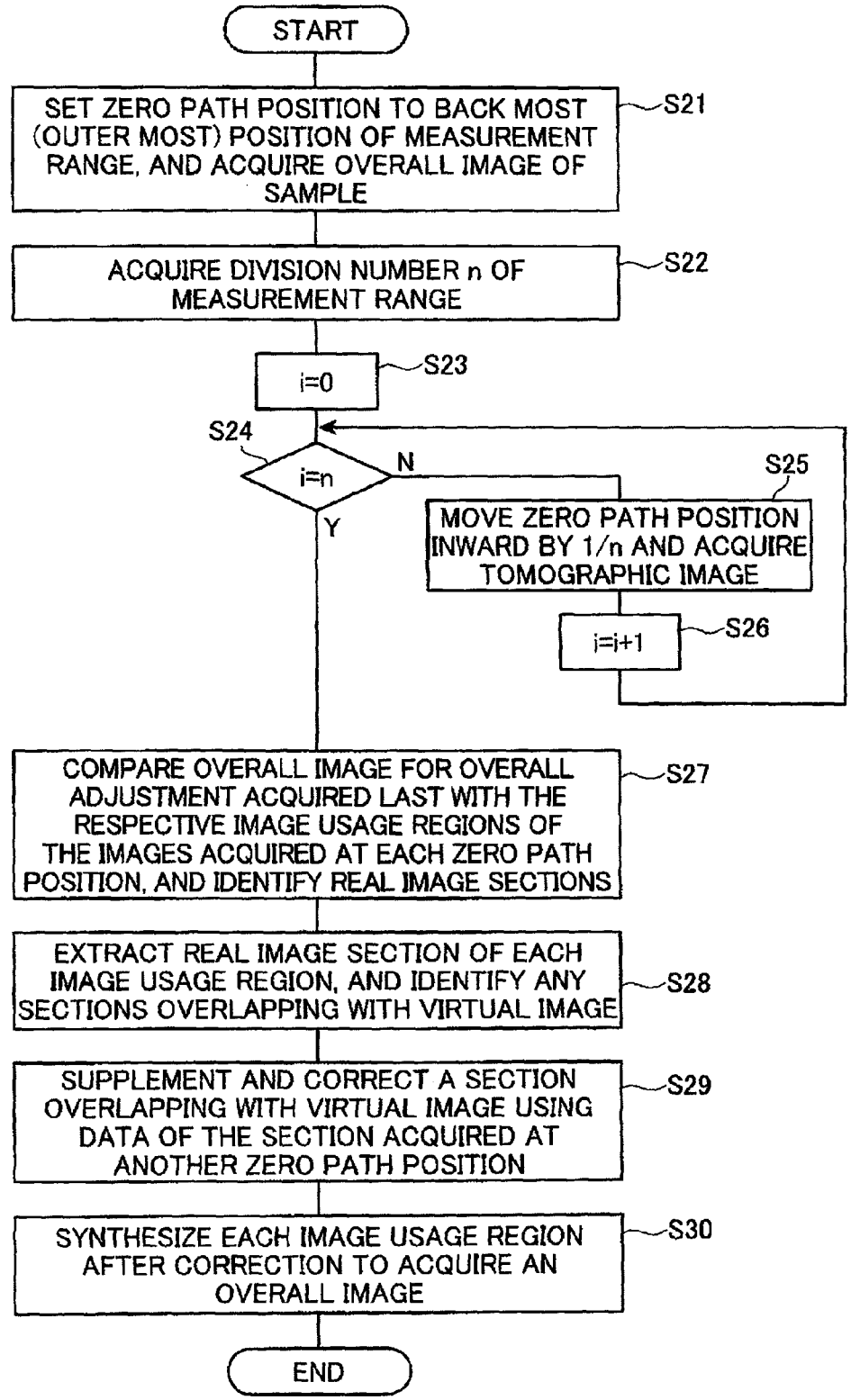
FIG. 14 is a flowchart illustrating an example of a tomographic image forming method of the fifth embodiment of the present invention.

FIG. 14 is a diagram illustrating the process flow of synthesized tomographic image formation of the processor 22C of the optical tomographic imaging system 10. FIGS. 15A to 15E are schematic diagrams illustrating display examples of the tomographic image of each switched zero path position, and graphs illustrating the FFT calculation results at one measuring position.

First, before measurement is started, the optical tomographic imaging system 10 is set to the initial zero path position setting. The initial zero path position setting is set by the control unit 32 controlling the optical path length adjustor 18. In this example, the first position of the zero path, which is set to the interior of the probe sheath 52, is established as the front most position of the measurement range. The control unit 32 drives the mirror moving mechanism 72 of the optical path length adjustor 18 of FIG. 1 so as to move the base 70 in the direction indicated by arrow A, thereby adjusting the optical path length so that the initial zero path position becomes the predetermined position in the interior of the probe sheath 52.

In the present embodiment, the optical path length switching unit 34 is set to the shortest optical path length (here, the fifth optical path length) for example when the zero path is set to the initial setting. This fifth optical path length corresponds to the initial zero path position (fifth zero path position Z5; refer to FIGS. 15A and 15E) set to the front most side of the object S.

After the fifth zero path position Z5 is set, the optical probe 16 is inserted into the body to be inspected and, once the optical probe 16 reaches the measurement area inside the body to be inspected, measurement is started. Subsequent processing will now be described following the flow shown in FIG. 14.

First, the control unit 32 controls the optical path length switching unit 34 so as to switch the optical path length to the longest optical path length (the first optical path length in the present embodiment), thereby switching the zero path position to the zero path position Z1 located farthest back in the measurement range (the first zero path position Z1; refer to FIG. 15A), performs optical measurement, and acquires an overall image of the measurement area across the entire region of the measurement range (step S21).

The tomographic image acquired in step S21 is displayed on the display 24. The left diagram of FIG. 15A shows a schematic view of the tomographic image acquired at the first zero path position Z1 that is displayed on the display 24. The right side of FIG. 15A shows the distribution of the signal intensity on the line 112, which is one measuring position in the rotational scanning direction of the entire measurement range acquired at the first zero path position Z1. In this graph, the first zero path position Z1 is shown as the origin point of the X axis. The peaks corresponding to the regions of interest S5 to S3 and the peaks corresponding to the outer periphery S2 and the inner periphery S1 of the probe sheath 52 appear in sequence, from the first zero path position Z1 toward the center.

Next, based on the displayed overall image, the operator inputs the division number n of the measurement range, i.e., the number of sections into which the measurement range is to be divided and measurement is to be performed, and the control unit 32 acquires and sends this division number n to the processor 22C (step S22). Here, as an example, the division number n is set to 4 and the division width is made equal so that the measurement range is divided into four equal sections.

The processor 22C then sets a counter i to 0 (step S23), moves the zero path position to the inside in increments by 1/n of the measurement range until i reaches the inputted division number n, and acquires tomographic images (steps S24 to S26). Specifically, the processor 22C switches the optical path length switching unit 34 to the optical path length corresponding to the second zero path position Z2 (here referred to as the second optical path length), thereby switching the zero path position from the first zero path position Z1 to the zero path position Z2 (referred to as the second zero path position Z2) located one position inward. Then, at the second zero path position Z2, a tomographic image is acquired in the same manner as at the first zero path position Z1. Subsequently, the counter i is increased by 1.

This process is repeated until i=n, and a tomographic image is similarly acquired at the zero path position Z3 located one position inward from the second zero path position Z2 (here referred to as the third zero path position Z3 corresponding to the third optical path length), and at the zero path position Z4 located one position inward from the third zero path position Z3 (here referred to as the fourth zero path position corresponding to the fourth optical path length).

Lastly, a tomographic image of the front most fifth zero path position Z5 is similarly acquired for overall adjustment.

Figure 15B:
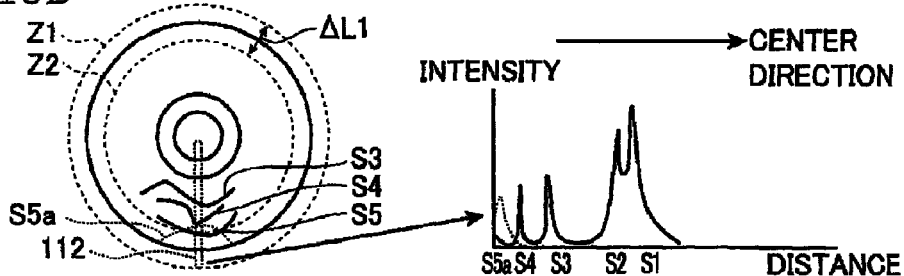

The left figure of FIG. 15B shows a schematic diagram of the tomographic image acquired at the second zero path position Z2. The right side of FIG. 15B shows a schematic graph of the distribution of the signal intensity on the line 112, from the center of the optical probe 16 to the region of interest S5. Here, the second zero path position Z2 is shown as the origin of the axis X, and the peaks corresponding to the regions of interest S4 and S3 and the peaks corresponding to the outer periphery S2 and the inner periphery S1 of the probe sheath 52 appear in order, from the second zero path position Z2 toward the center.

The signal intensity obtained by the tomographic information generating means 84 was obtained upon performing FFT processing on the interference signal. As a result, on both sides of the zero path, the interference signals detected at positions of equal distance from the zero path position appear as overlapped information. In the right figure of FIG. 15B, the region of interest S5 is located right next to the side (outside) of the second zero path position Z2 that is not subject to measurement, causing the peak corresponding to the region of interest S5 to appear as a virtual image as a region of interest S5a.

Figure 15C:
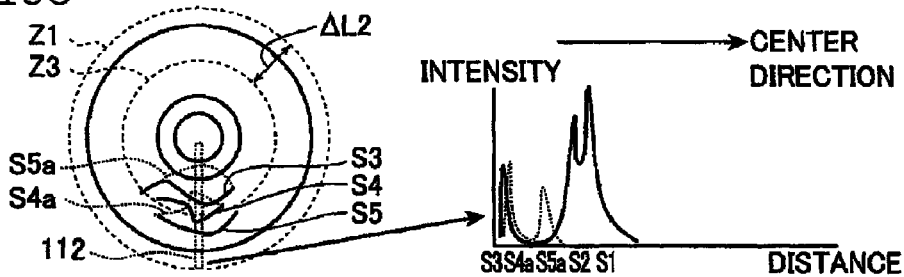
Figure 15D:
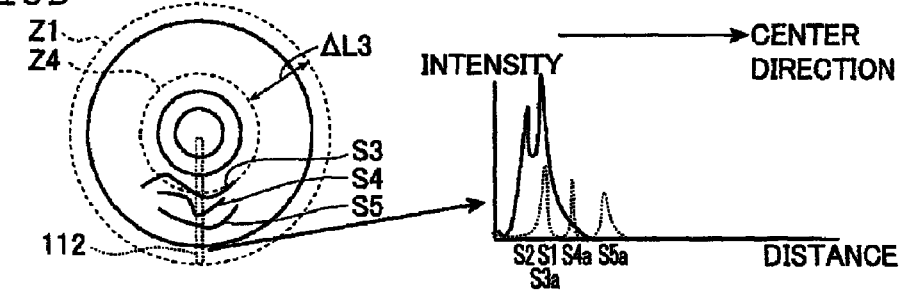

In FIG. 15C, which is a schematic diagram of the tomographic image acquired at the third zero path position Z3, and FIG. 15D, which is a schematic diagram of the tomographic image acquired at the fourth zero path position Z4, as well, regions of interest S5a, S4a, and S3a which are virtual images similarly appear owing to the relationship with the respective zero path positions.

Figure 15E:
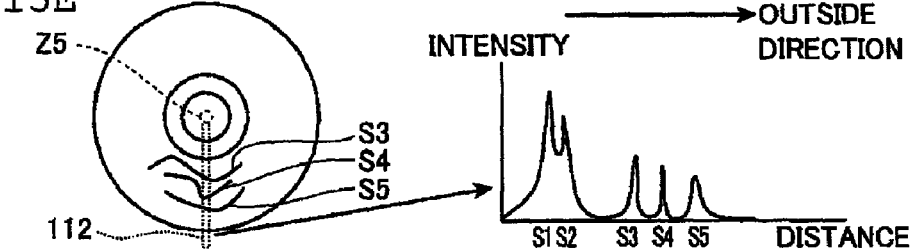

FIG. 15E shows a schematic diagram of the tomographic image acquired at the fifth zero path position Z5. This zero path position is the front most position and thus the outside of the zero path is considered as a region to be measured. Accordingly, the schematic diagram of the signal distribution is exactly opposite the schematic diagram of the signal distribution acquired at the first zero path position Z1. Furthermore, the zero path position is located at the substantial center of the probe and therefore no virtual images appear.

Next, the processor 22C performs processing in the tomographic image generating means 86 to remove the reflection of the virtual images that appear in the tomographic images acquired at the second zero path position Z2 to the fourth zero path position Z4. First, the processor 22C compares the overall image for overall adjustment that was lastly acquired at the zero path position Z5 and is free of virtual image reflection, with the image usage regions of the images acquired at each zero path position from the second zero path position Z2 to the fourth zero path position Z4, and identifies the real image sections (step S27).

Figure 16A:
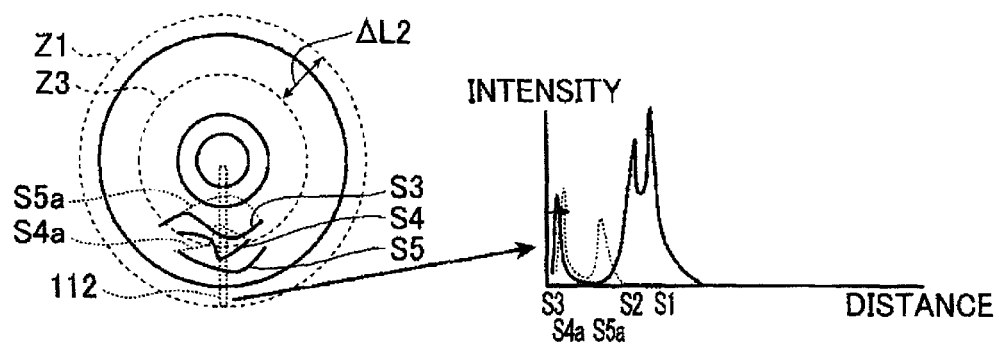
FIG. 16A to FIG. 16C are explanatory views illustrating an example of a false signal identification method of the fifth embodiment of the present invention.
Figure 16B:
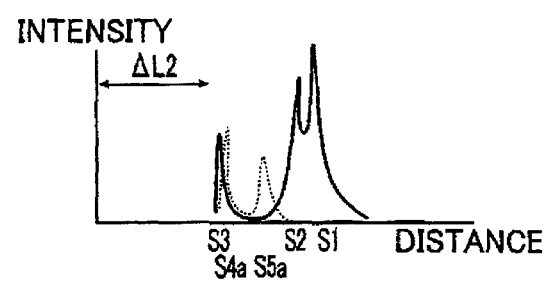
Figure 16C:
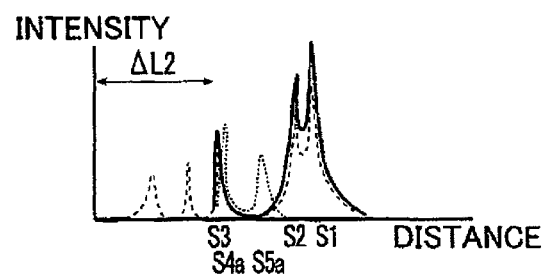
Figure 17A:
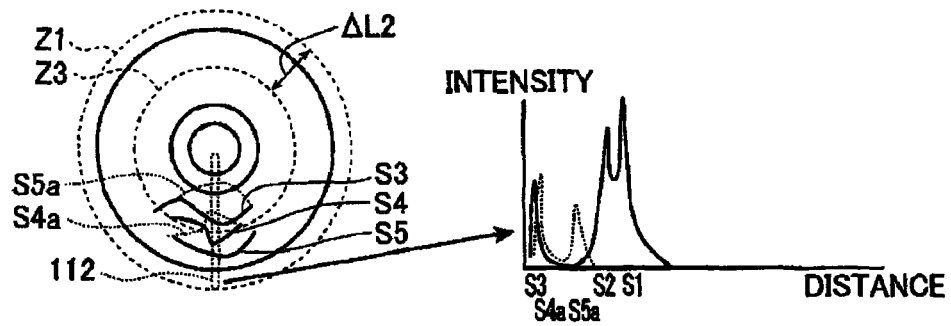
FIG. 17A to FIG. 17E are explanatory views illustrating an example of a real image section extraction method of the fifth embodiment of the present invention.
Figure 17B:
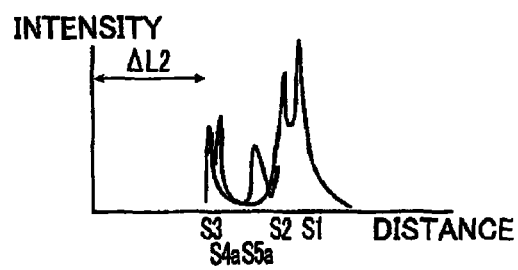
Figure 17C:
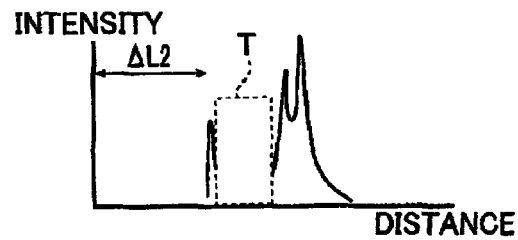
Figure 17D:
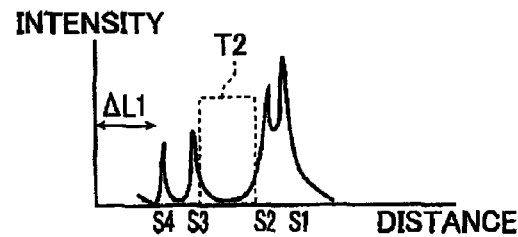
Figure 17E:
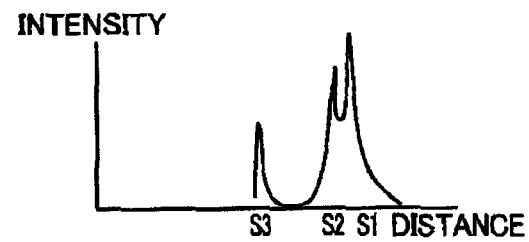
Figure 18A:
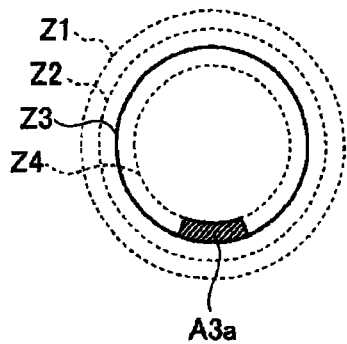
FIG. 18A and FIG. 18B are explanatory views illustrating an example of a correction area of the fifth embodiment of the present invention.
Figure 18B:
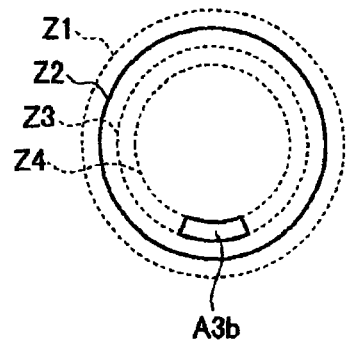
Figure 20A:
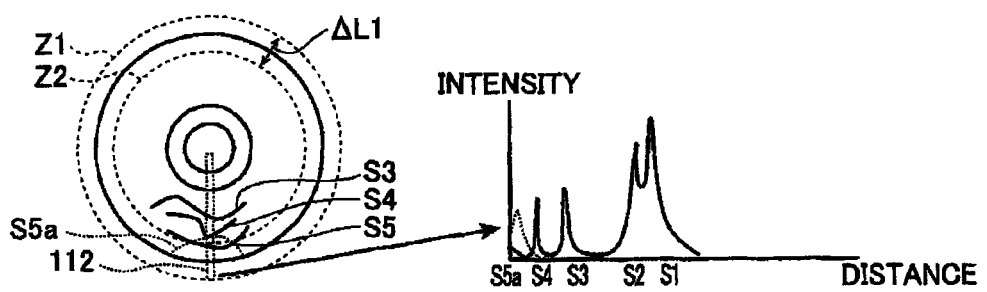
FIG. 20A and FIG. 20B are explanatory views illustrating another example of a false signal identification method of the sixth embodiment of the present invention.
Figure 20B:
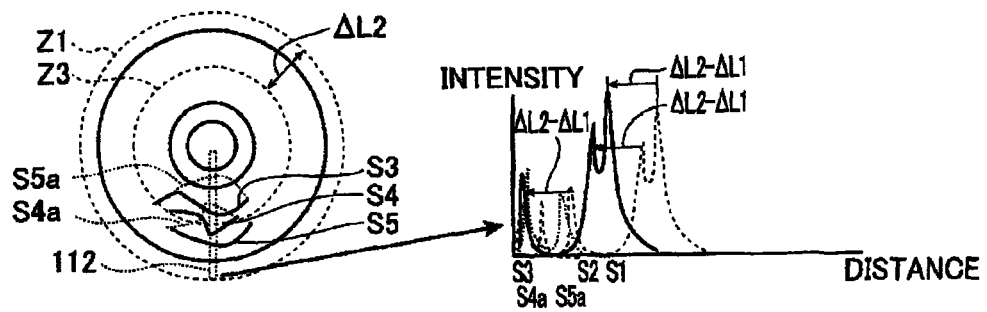

As an example, FIG. 16 illustrates a method for identifying the real image section in the case of the third zero path position Z3 shown in FIG. 15C. In the third zero path position Z3, the interference signals corresponding to the regions of interest S4 and S5 are virtual images and are expressed as regions of interest S4a and S5a, as shown in FIG. 16A. The third zero path position Z3 is a zero path position moved by an amount equivalent to $\Delta L2$ from the first zero path position Z1 that serves as the reference position. As a result, as shown in FIG. 16B, the interference signal is offset by an amount of movement equivalent to $\Delta L2$. Then, the signal distribution (refer to the right figure of FIG. 15E) of the interference signal of the fifth zero path position for overall adjustment is inverted and superimposed onto FIG. 16B, making it possible to compare the interference signal of the fifth zero path position Z5 and the interference signal of the third zero path position Z3 in a schematic diagram of the signal distribution of the interference signal, as shown in FIG. 16C.

As a result, the peaks where the coordinates of the X axis match, i.e., the probe inner periphery S1, the probe outer periphery S2, and the region of interest S3, are true signals, and the peaks where the coordinates of the X axis do not match, i.e., the regions of interest S4a and S5a, are false signals, making it possible to identify these regions as virtual images. Additionally, the sections where a peak appears as a double peak can be identified as sections where true and false signals overlap.

After real image section identification, the real image sections identified in the step S27 of the image usage regions A1 to A4 shown in FIG. 15A are extracted, and the sections that overlap with virtual images are identified (step S28). Next, the sections identified as overlapping with virtual images are supplemented and corrected using the data of application sections acquired at other zero path positions (step S29). In the example of FIG. 16, surrounding areas of the signal of the regions of interest S4a and S5a identified as virtual images overlap with each other. As a result, the sections overlapping between the regions of interest S4a and S5a, including arbitrary peripheral regions, are subject to correction.

FIG. 17 illustrates the supplementation and correction method of the sections that overlap with virtual images in the example of FIG. 15C, which was subjected to real image section identification above. First, the original interference signal shown in FIG. 17A is offset by an amount of movement equivalent to ΔL2 of the third zero path position Z3, as shown in FIG. 17B. Next, as shown in FIG. 17C, a correction area T, which includes arbitrary peripheral regions including the signals of the regions of interest S4a and S5a identified as virtual images, is set. Then, the correction area T is corrected by extracting a section T2 corresponding to the correction area T of another zero path position, for example, the section T2 of FIG. 17D where the interference signal acquired at the second zero path position Z2 shown in FIG. 15B was offset by ΔL1, supplementing the correction area T using the signal of the area T2 of FIG. 17D as shown in FIG. 17E, and smoothly connecting the sections in back and in front of the correction area T.

Here, the regions of interest S4a and S5a identified as virtual images are not necessarily reflected on all lines in the circumferential direction, but rather on some of the lines only. Thus, the above-described correction just needs to be performed only on the lines where a section that overlaps with a region of interest identified as a virtual image exists. For example, in a case where a virtual image is reflected only in area A3a shown in FIG. 18A, which is a schematic diagram of the tomographic image acquired at the third zero path position Z3, only the lines that contain the area A3a need to be supplemented and corrected using the area A3a shown in FIG. 18B, which is a schematic diagram of the tomographic image acquired at the second zero path position Z2.

With this arrangement, it is possible to obtain a high-resolution tomographic image for lines free of virtual image reflection as well as an overall high-resolution tomographic image that is free of virtual image reflection for lines that contain virtual image reflection and have a slightly lower resolution that those free of virtual image reflection.

The image usage regions at each zero path position acquired through the steps until step S29 and from which real image sections were extracted are then synthesized by the image synthesizing means 88 (step S30).

While the image usage regions in this example were selected from the images of each zero path position for image synthesizing and then synthesized, the overall synthesized image may be acquired by weighting the entire image of each zero path position. In such a case, supplementation may be performed by using not only the section of the correction area T2 corresponding to the correction area T, but also the data of the entire region including the correction area T2 acquired at the second zero path position Z2.

Further, the image usage regions to be synthesized may overlap. For example, the area A3 of the tomographic image acquired at the third zero path position Z3 is also acquired at the second zero path position Z2, making it possible to obtain a synthesized tomographic image using the tomographic images of both zero path positions.

While in the above the tomographic image of the fifth zero path position Z5 acquired last was used as a comparison tomographic image for identifying real images, the tomographic image of the first zero path position Z1 acquired first may be used for comparison. Additionally, while the tomographic images were acquired in order starting from the back most first zero path position Z1, the tomographic images may be acquired starting from the front most fifth zero path position Z5. Additionally, while the inside of the zero path was established as the image usage region in the above, the outside of the zero path may be established as the image usage region as well.

Figure 19:
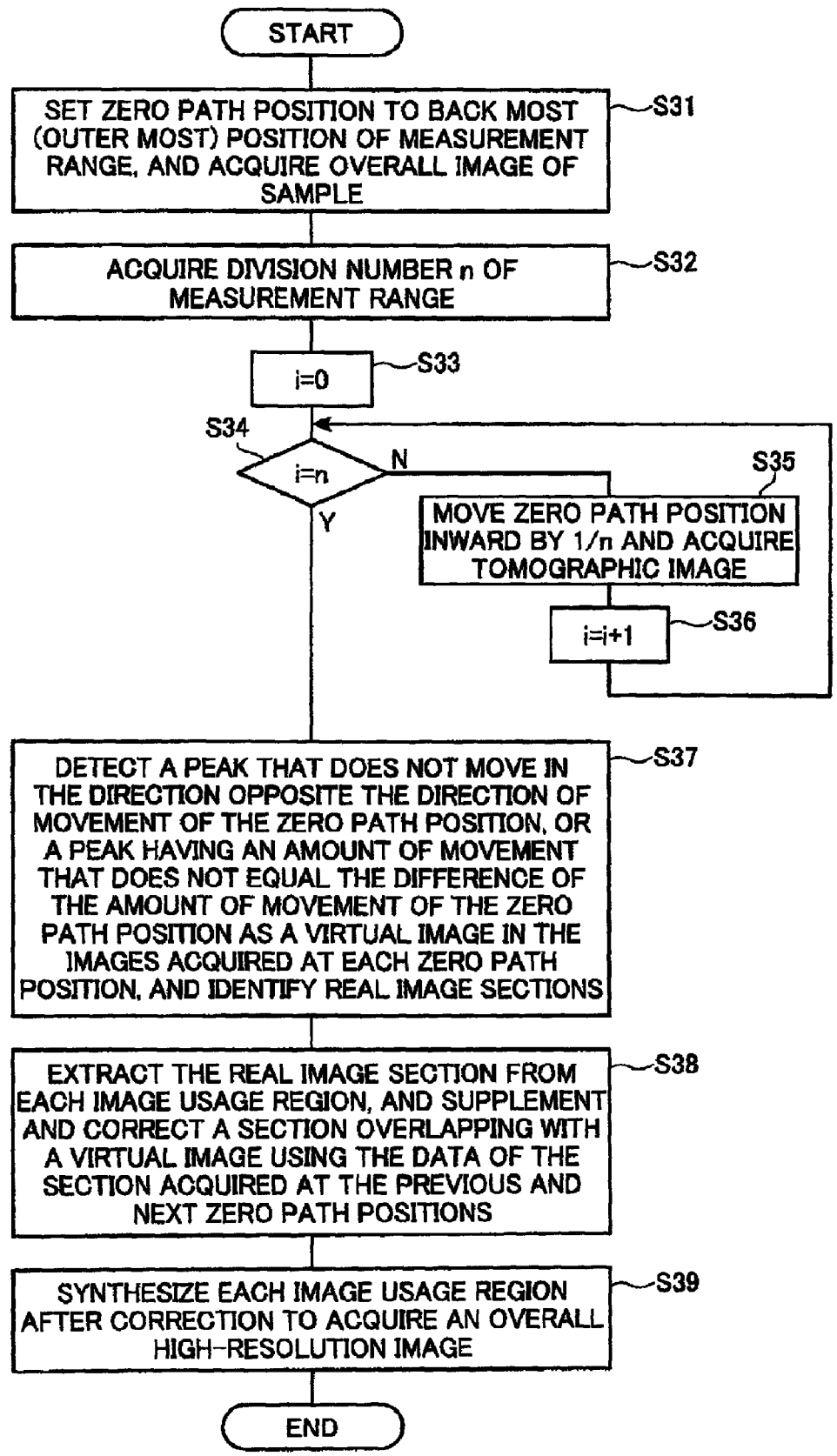
FIG. 19 is a flowchart illustrating the processing of the sixth embodiment of an optical tomographic imaging system according to the present invention.

Next, the sixth embodiment of the present invention will be described. In the sixth embodiment of the present invention, the same optical tomographic imaging system 10 as in the above detects the virtual images that occur when the zero path position is an intermediate position using a different method, and identifies the real image sections using a different method. FIG. 19 is a flowchart illustrating the processing of this sixth embodiment. The method in which the tomographic image is acquired at each zero path position (steps S31 to S36) is the same as that of the fifth embodiment, and a detailed description thereof will be omitted. The virtual image detection method and real image section identification method will now be described.

In the images acquired at each zero path position, the peak corresponding to each region of interest moves in accordance with the amount of movement of the zero path position, as described in FIG. 15 of the aforementioned fifth embodiment. At the third zero path position Z3 shown in FIG. 20B, the zero path position moves forward from the previous second zero path position Z2 shown in FIG. 20A. Then, as shown in the right figure of FIG. 20B, the regions of interest S1 to S3, which are true signals, move backward, i.e., toward the origin point of the X axis, by an amount equivalent to the amount of movement of the zero path position, i.e., by ΔL2−ΔL1, as seen in the graph of the interference signal.

However, the region of interest S5a, which is a false signal or virtual image, moves forward in the direction away from the origin point of the X axis. In this manner, all peaks other than the peaks that move in the direction opposite the direction of movement of the zero path position on the graph of the interference signal are detected as virtual images (step S37).

Additionally, while the region of interest S4a, which is a virtual image, moves in the direction opposite the direction of movement of the zero path position on the graph of the interference signal, the amount of movement does not equal ΔL2−ΔL1. In such a case as well, the peak is detected as a peak that crosses the zero path position and is reflecting as a virtual image (step S37).

The real image sections from the peaks detected as such virtual images are thus identified.

After real image section identification, the real image sections identified in the step S37 of each image usage region are extracted, and the sections that overlap with the virtual images are identified (step S38). Surrounding areas of the signal of the regions of interest S4a and S5a identified as virtual images include real image and virtual image overlapping with each other. As a result, the sections overlapping with the regions of interest S4a and S5a, including arbitrary peripheral regions, are established as sections to be corrected, and supplementation and correction are performed (step S38).

Here, the details of identification of sections overlapping with virtual images, and the supplementation and correction method are the same as those of the aforementioned fifth embodiment.

The image usage regions at each zero path position acquired in step S38 and from which real image sections were extracted are then synthesized by the image synthesizing means 88 (step S39). The synthesized tomographic image is then sent to the image quality correcting means 90 and subjected to image processing for display, such as radial processing, sharpening processing, and the like. Subsequently, the tomographic image is sent to the display 24 and displayed.

Here, similar to the fifth embodiment, various imaging synthesizing methods are used to obtain an overall high-resolution tomographic image.

Next, the seventh embodiment of the optical tomographic imaging system of the fourth aspect of the present invention will be described.

FIG. 6 previously used to describe the second embodiment of the optical tomographic imaging system of the first aspect of the present invention can be similarly used when describing the optical tomographic imaging system of the fourth aspect of the present invention. Thus, FIG. 6 is a block diagram schematically illustrating the configuration of the seventh embodiment of the optical tomographic imaging system of the fourth aspect of the present invention.

The optical tomographic imaging system 100 of the seventh embodiment of the present invention that is shown in FIG. 6 is the same as the optical tomographic imaging system 10 of the fifth embodiment of the present invention that is shown in FIG. 1, but further comprises the parameter storing unit 38. Note that all other elements or constituents have basically the same configuration as that of the optical tomographic imaging system 10, equivalent elements or constituents are denoted using the same reference numerals, and the detailed descriptions thereof will be omitted. The following mainly describes the differences between the optical tomographic imaging system 100 of the seventh embodiment of the present invention and the optical tomographic imaging system 10 of the fifth embodiment of the present invention described earlier.

Note that the parameter storing unit 38, which is one difference between the optical tomographic imaging system 100 shown in FIG. 6 and the optical tomographic imaging system 10 shown in FIG. 1, has been previously described in the second embodiment with reference to FIG. 6, and the same description thereof will be omitted.

As described above, the OCT system configured to acquire information of the tomographic image by low coherence light is capable of acquiring a high resolution image as the distance from the zero path position decreases, but the image quality deteriorates as the distance from the zero path position increases. Thus, the number of times n the measurement range is switched (hereinafter "switching count n") in order to obtain a high-resolution image of the region of interest differs according to the measurement area and the region of interest.

Based on the above, the optical tomographic imaging system 100 presets the position parameters of each zero path position and the switching count n, i.e., the division count n, in accordance with the respective measurement areas, and stores these values in the parameter storing unit 38. Furthermore, each zero path position parameter and switching count n corresponding to the depth range of the region of interest are preferably stored in the parameter storing unit 38 for each of the respective measurement areas.

The position parameters of the zero path position may be set as, for example, each zero path position in terms of the initial setting (first reference position) of the zero path, suitable for measuring that region of interest, in accordance with a certain measurement region and, moreover, the depth of that region of interest; or the zero path position set at the edge (inner edge or outer edge) of the measurement range on the side opposite the initial position (first reference position) of the zero path, and the number of zero paths to be set between the first reference position and the second reference position (the zero path position on the inner edge and the zero path position on the outer edge).

A plurality of optical paths with optical path lengths corresponding to the zero path position parameters are prepared in the optical path length switching unit 34, making it possible to switch the optical path in accordance with the parameters and the switching count n. Or, the optical path length switching unit 34 comprises a configuration that makes it possible to arbitrarily switch the optical path length in accordance with the zero path position parameters and the switching count n.

In a case where the configuration makes it possible for the optical path length switching unit 34 to arbitrarily change the optical path length, the parameters stored in the parameter storing unit 38 may be freely set by the operator. Additionally, the switching positions of each zero path position may be simply prepared in stages and the parameters corresponding to each position and the switching count n may be stored in the parameter storing unit 38 so that each zero path position and switching count n are switched when the operator selects the range of depth of the region of interest.

The tomographic image forming method of the optical tomographic imaging system 100 will now be described with reference to FIG. 21. When measurement begins, the zero path position is set to the back most side of the measurement range, and an overall image of the measurement range is acquired (step S51). The optimum parameters and switching count n are acquired from the parameter storing unit 38 based on the measurement area or region of interest inputted by the operator and the acquired overall image (step S52).

Subsequently, processing equivalent to steps S13 to S20 of the fifth embodiment are performed in steps S53 to S60, thereby making it possible to obtain a high-resolution tomographic image that synthesizes the tomographic images of the switching count n acquired from the parameter storing unit 38.

Or, processing equivalent to steps S33 to S39 of the sixth embodiment may be performed so as to obtain a high-resolution tomographic image that synthesizes the tomographic images of the switching count n acquired from the parameter storing unit 38.

The parameters and switching count n are thus maintained according to the measurement area and the region of interest, making it possible to easily switch the zero path position according to the measurement area and region of interest. Additionally, the zero path position can be easily switched even in a case where the measurement area and region of interest are changed during measurement, making it possible to perform measurement more quickly and further improve the user-friendliness of the optical tomographic imaging system.

Further, while the above describes an embodiment wherein the zero path position is switched by switching the optical path length of the reference light L2 as a preferred embodiment, the optical path length of the measuring light L1 may be switched so as to switch the zero path position as well.

Note that while the present invention has been described in detail above, the present invention is not limited to the aforementioned embodiments, and various modifications may be made without departing from the spirit and scope of the invention.

What is claimed is:

1. An optical tomographic imaging system comprising:
   a wavelength-swept light source;
   a splitter configured to split light emitted from said wavelength-swept light source into measuring light and reference light;
   an optical probe configured to irradiate said measuring light from said splitter onto a measuring object to be measured and contain within a sheath a measuring unit that acquires reflected light from said measuring object;
   an optical path length adjustor configured to set a first reference position of a measurement depth direction to an inner edge of a measurement range by adjusting an optical path length of said reference light;
   an optical path length switching unit that has a preset optical path length that differs from said first reference position in terms of measurement depth by a predetermined amount and provides a second reference position on an outer edge of the measurement range, and is configured to change the optical path length of said reference light or the optical path length of said reflected light adjusted by said optical path length adjustor so as to switch between said first reference position and said second reference position;
   a control unit configured to control said optical path length adjustor and said optical path length switching unit;
   a multiplexer configured to multiplex a reflected light and said reference light acquired by said measuring unit and generate an interference light, disposed on a downstream side of said optical path length adjustor and said optical path length switching unit;
   an interference light detector configured to detect said interference light generated by said multiplexer as an interference signal; and
   a tomographic image acquiring and processing unit configured to obtain a tomographic image from said interference signal detected by said interference light detector.

2. The optical tomographic imaging system according to claim 1, wherein:
   said control unit switches said optical path length switching unit to said first reference position and said second reference position during measurement by said measuring unit; and
   said tomographic image acquiring and processing unit acquires two tomographic images for an identical measuring object based on both said first reference position and said second reference position switched by said optical path length switching unit.

3. The optical tomographic imaging system according to claim 2, wherein:
   said control unit switches said optical path length switching unit to said first reference position and said second reference position in synchronization with a rotational scanning period or a flatbed scanning period of said measuring unit during measurement by said measuring unit; and
   said tomographic image acquiring unit synthesizes an entire tomographic image or a part of said first reference position side of a tomographic image based on said first reference position, and an entire tomographic image or a part of said second reference position side of a tomographic image based on said second reference position so as to obtain a synthesized tomographic image.

4. The optical tomographic imaging system according to claim 1, wherein said optical path length switching unit comprises plural optical path lengths as the optical path length that provide said second reference position.

5. The optical tomographic imaging system according to claim 4, further comprising:
   a parameter storing unit configured to maintain parameters of said second reference position preset per measurement area; wherein:
   said control unit reads parameters of said second reference position from said parameter storing unit in accordance with inputted measurement area information, and switches the optical path length of said optical path length switching unit in accordance with said read parameters.

6. The optical tomographic imaging system according to claim 5, wherein:
   said parameter storing unit stores plural parameters as one set of measurement area information; and
   said control unit reads the parameters of said second reference position in accordance with inputted instruction information, and switches the optical path length of said optical path length switching unit in accordance with said read parameters.

7. A tomographic image acquiring method in said optical tomographic imaging system according to claim 5, further comprising:
   reading parameters of said second reference position from said parameter storing unit based on inputting of measurement area information; and
   switching the optical path length of said optical path length switching unit in accordance with said read parameters.

8. The optical tomographic imaging system according to claim 1, wherein:
   said tomographic image acquiring and processing unit further comprises a detector configured to detect a distance between a tip of said optical probe and the measuring object; and
   said control unit switches the optical path length said optical path length switching unit to an optical path corresponding to said first reference position when a distance between the tip of said optical probe and the measuring object that was detected by said tomographic image acquiring and processing unit is greater than or equal to a predetermined distance.

9. The optical tomographic imaging system according to claim 8, wherein said control unit adjusts the optical path length of said optical path length switching unit or said optical path length adjustor so that said first reference position aligns with a front surface of the measuring object that is nearest to an inner edge of said measurement range when the distance between the tip of said optical probe and the measuring object that is detected by said tomographic image acquiring and processing unit is greater than or equal to a predetermined distance.

10. The optical tomographic imaging system according to claim 9, wherein:
    said optical probe further comprises a drive unit configured to rotate said measuring unit and an optical fiber configured to transmit said measuring light to said measuring unit and said reflected light from said measuring unit; and
    said tomographic image acquiring and processing unit is configured to obtain a two-dimensional tomographic image of a circular shape corresponding to rotation of said measuring unit and, from an adjustment amount of said first reference position and a distance between said first reference position after adjustment and a center of a tomographic image obtained at said first reference position before adjustment, correct a tomographic image obtained based on said first reference position after said adjustment.

11. The optical tomographic imaging system according to claim 1, wherein said optical path length switching unit further has plural optical paths of different lengths and switching means for switching said plural optical paths.

12. The optical tomographic imaging system according to claim 11, wherein said image synthesizer weights said plural tomographic images in whole or in part, and synthesizes the weighted tomographic images.

13. The optical tomographic imaging system according to claim 1, wherein said optical path length switching unit shifts optical path length adjusting means of said optical path length adjustor so as to switch the optical path to one of plural optical path lengths.

14. A tomographic image acquiring method in said optical tomographic imaging system according to claim 1, comprising:
switching, when said first reference position or said second reference position is selected in accordance with a measurement region of interest, said optical path length switching unit to said selected reference position; and
acquiring a tomographic image based on said switched reference position.

15. The optical tomographic image acquiring method according to claim 14, further comprising the steps of:
detecting a distance between the tip of said optical probe and the measuring object; and
automatically selecting said first reference position when a detected distance between a tip of said optical probe and the measuring object is greater than or equal to a predetermined distance.

16. The tomographic image acquiring method according to claim 15, further comprising a step of adjusting said optical path length adjustor so that said first reference position is aligned with a front surface of the measuring object that is nearest to an inner edge of said measurement range when a detected distance between the tip of said optical probe and the measuring object is greater than or equal to a predetermined distance.

17. The tomographic image acquiring method according to claim 16, further comprising the step of correcting, from an adjustment amount of said first reference position and a distance between said first reference position after adjustment and a center of a tomographic image obtained at said first reference position before adjustment, a tomographic image obtained based on said first reference position after said adjustment so as to generate an image similar to a tomographic image obtained at said first reference position before adjustment, in a case where a two-dimensional tomographic image of a circular shape corresponding to rotation of said measuring unit is to be obtained.

18. A tomographic image acquiring method in said optical tomographic imaging system according to claim 1, comprising:
switching said optical path length switching unit to each of said first reference position and said second reference position during measurement by said measuring unit; and
acquiring two tomographic images for the same measuring object based on both said first reference position and said second reference position.

19. The optical tomographic image acquiring method according to claim 18, further comprising:
switching said optical path length switching unit to each of said first reference position and said second reference position in synchronization with a rotational scanning period or a flatbed scanning period of said measuring unit, during measurement by said measuring unit; and
synthesizing a part of said first reference position side of a tomographic image based on said first reference position and a part of said second reference position side of a tomographic image based on said second reference position so as to obtain a synthesized tomographic image.

20. An optical tomographic image forming method based on optical tomographic image measurement using a wavelength-swept light source, comprising:
setting a first reference position of a measurement depth direction to an inner edge or an outer edge of a measurement range;
setting plural reference positions, each having a measurement depth differing from that of said first reference position; acquiring plural tomographic images based on said first reference position and said plural reference positions for the same measuring object; and
synthesizing regions of said plural tomographic images in whole or in part so as to form a single synthesized tomographic image.

21. The optical tomographic imaging forming method according to claim 20, wherein said step of synthesizing said plural tomographic images includes the synthesizing of regions near said reference position of each tomographic image.

22. The optical tomographic image forming method according to claim 20, after said plural tomographic images based on said plural reference positions are acquired, further comprising:
identifying for each of said plural tomographic images a false signal included in the signal of said tomographic image, based on the signal of a region on the side opposite said reference position;
obtaining a real signal by removing said false signal from the signal of said tomographic image;
generating a real image by said real signal of said tomographic image; and
forming said synthesized tomographic image using said real images of said plural tomographic images.

23. The optical tomographic image forming method according to claim 22, wherein the step of identifying said false signal is performed by comparing each of plural tomographic images based on said plural reference positions with a tomographic image based on said first reference position, and identifying a signal that does not exist in a tomographic image based on said first reference position as a false signal.

24. The optical tomographic image forming method according to claim 22, wherein said step of identifying said false signal is performed by comparing two of said tomographic images based on said reference positions located next to each other, and identifying a signal that moves an amount equivalent to double an amount of shift of said reference position in the same direction as the direction of shift of said reference position, or a signal other than a signal that shifts in the direction opposite the direction of shift of said reference position as a false signal.

25. The optical tomographic image forming method according to claim 20, further comprising said step of weighting said plural tomographic images in whole or in part, and synthesizing the weighted tomographic images.

26. The optical tomographic image forming method according to claim 20, wherein a range of said tomographic image to be used in said synthesized tomographic image is arbitrarily set in accordance with the measuring object.

27. The optical tomographic image forming method according to claim 20, further comprising:
reading the position parameters of said plural reference positions corresponding to said inputted measurement area information; and
setting said plural reference positions based on said read position parameters, wherein the position parameters of said plural reference positions for acquiring said plural tomographic images are pre-stored per measurement area.

28. The optical tomographic image forming method according to claim 27, wherein:
said plural reference positions include a second reference position at an outer edge or an inner edge of a measurement range; and
said second reference position and the number of said reference positions set between said first reference position and said second reference position are stored as said position parameters.

29. An optical tomographic imaging system, comprising:
a wavelength-swept light source;
a splitter configured to split light emitted from said wavelength-swept light source into measuring light and reference light;
an optical probe configured to irradiate said measuring light from said splitter onto a measuring object and contain within a sheath a measuring unit that acquires reflected light from the measuring object;
an optical path length adjustor configured to set a first reference position of a measurement depth direction to an inner edge of a measurement range by adjusting an optical path length of said reference light;
an optical path length switching unit having preset plural optical path lengths that provide plural reference positions that differ from said first reference position in terms of measurement depth, and configured to change the optical path length of said reference light or the optical path length of said reflected light adjusted by said optical path length adjustor so as to switch to said first reference position or one of said plural reference positions;
a control unit configured to control said optical path length switching unit so as to switch to said first reference position and one of said plural reference positions in synchronization with a rotational scanning period or a flatbed scanning period of said measuring unit, during measurement by said measuring unit;
a multiplexer configured to multiplex a reflected light and said reference light acquired by said measuring unit and generate an interference light, disposed on a downstream side of said optical path length adjustor and said optical path length switching unit;
an interference light detector configured to detect said interference light generated by said multiplexer as an interference signal;
a tomographic image generator configured to generate plural tomographic images respectively based on said first reference position and said plural reference positions switched by said optical path length switching unit, from said interference signal detected by said interference light detector; and
an image synthesizer configured to synthesize said plural tomographic images acquired by said tomographic image generator in whole or in part and form a single synthesized tomographic image.

30. The optical tomographic imaging system according to claim 29, wherein said image synthesizer synthesizes said plural tomographic images so as to include regions near said reference position of each tomographic image.

31. The optical tomographic imaging system according to claim 29, wherein:
said tomographic image generator identifies for each of plural tomographic images based on said plural reference positions a false signal that is included in the signal of said tomographic image and is based on the signal of a region on the side opposite said reference position, and generates a real image by a real signal after said false signal is removed from the signal of said tomographic image; and
said image synthesizer synthesizes said plural tomographic images using said real images of said plural tomographic images generated by said tomographic image generator.

32. The optical tomographic imaging system according to claim 31, wherein said tomographic image generator identifies said false signal by comparing each of plural tomographic images based on said plural reference positions with a tomographic image based on said first reference position, and identifying a signal that does not exist in a tomographic image based on said first reference position as a false signal.

33. The optical tomographic imaging system according to claim 31, wherein said tomographic image generator identifies said false signal by comparing two of said tomographic images based on said reference positions located next to each other, and identifying a signal that moves an amount equivalent to double the amount of shift of said reference position in the same direction as the direction of shift of said reference position, or a signal other than a signal that shifts in the direction opposite the direction of shift of said reference position as a false signal.

34. The optical tomographic imaging system according to claim 29, wherein the range of said tomographic image to be used in said synthesized tomographic image is arbitrarily set in accordance with a measuring object.

35. The optical tomographic imaging system according to claim 29, further comprising a parameter storing unit configured to store position parameters of said plural reference positions preset per measurement area, wherein:
said control unit reads the position parameters of said plural reference positions from said parameter storing unit in accordance with inputted measurement area information, and switches the optical path length of said optical path length switching unit in accordance with said read position parameters.

36. The optical tomographic imaging system according to claim 35, wherein said plural reference positions include a second reference position at an outer edge or an inner edge of a measurement range, and said parameter storing unit stores as said position parameters said second reference position and the number of said reference positions between said first reference position and said second reference position.

* * * * *